(12) United States Patent
Zhan et al.

(10) Patent No.: US 7,740,840 B1
(45) Date of Patent: Jun. 22, 2010

(54) **HIGH ACTIVITY MUTANTS OF BUTYRYLCHOLINESTERASE FOR COCAINE H

HIGH ACTIVITY MUTANTS OF BUTYRYLCHOLINESTERASE FOR COCAINE HYDROLYSIS

RELATED APPLICATIONS

This application is a continuation-in-part of co-pending U.S. patent application Ser. No. 12/192,394 filed Aug. 15, 2008, which is a divisional of U.S. patent application Ser. No. 11/243,111, filed Oct. 4, 2005 and now issued as U.S. Pat. No. 7,438,904. The entire disclosures contained in U.S. patent application Ser. No. 12/192,394, U.S. patent application Ser. No. 11/243,111, and U.S. Pat. No. 7,438,904 are incorporated herein by this reference.

GOVERNMENT INTEREST

Subject matter described herein was made with government support under Grant Number R01DA013930 awarded by the National Institute on Drug Abuse (NIDA) of the National Institutes of Health (N1H). The government has certain rights in the described subject matter.

TECHNICAL FIELD

The presently-disclosed subject matter relates to butyrylcholinesterase variant polypeptides, and in particular, butyrylcholinesterase mutants having amino acid substitutions.

INTRODUCTION

Cocaine abuse is a major medical and public health problem that continues to defy treatment. The disastrous medical and social consequences of cocaine addiction, such as violent crime, loss in individual productivity, illness, and death, have made the development of an effective pharmacological treatment a high priority. However, cocaine mediates its reinforcing and toxic effects by blocking neurotransmitter reuptake and the classical pharmacodynamic approach has failed to yield small-molecule receptor antagonists due to the difficulties inherent in blocking a blocker. An alternative to receptor-based approaches is to interfere with the delivery of cocaine to its receptors and accelerate its metabolism in the body.

The dominant pathway for cocaine metabolism in primates is butyrylcholinesterase (BChE)-catalyzed hydrolysis at the benzoyl ester group (Scheme 1).

Scheme 1. Schematic representation of BChE-catalyzed hydrolysis at the benzoyl ester group.

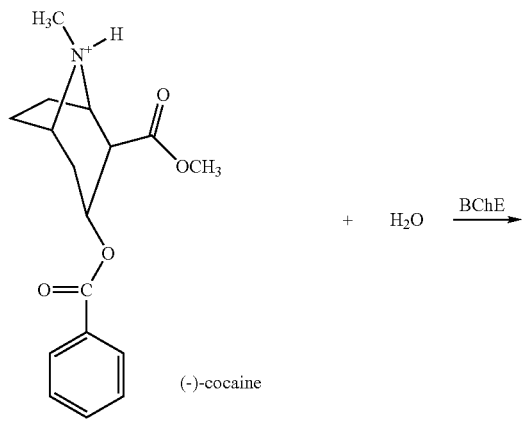

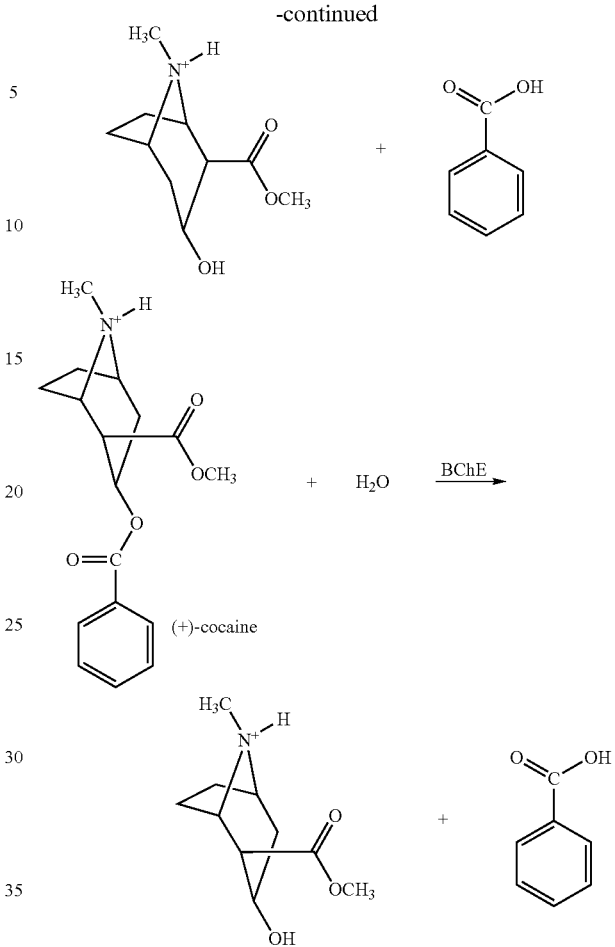

Only 5% of the cocaine is deactivated through oxidation by the liver microsomal cytochrome P450 system. Cocaine hydrolysis at benzoyl ester group yields ecgonine methyl ester, whereas the oxidation produces norcocaine. The metabolite ecgonine methyl ester is a biologically inactive metabolite, whereas the metabolite norcocaine is hepatotoxic and a local anesthetic. BChE is synthesized in the liver and widely distributed in the body, including plasma, brain, and lung. Extensive experimental studies in animals and humans demonstrate that enhancement of BChE activity by administration of exogenous enzyme substantially decreases cocaine half-life.

Enhancement of cocaine metabolism by administration of BChE has been recognized to be a promising pharmacokinetic approach for treatment of cocaine abuse and dependence. However, the catalytic activity of this plasma enzyme is three orders-of-magnitude lower against the naturally occurring (−)-cocaine than that against the biologically inactive (+)-cocaine enantiomer. (+)-cocaine can be cleared from plasma in seconds and prior to partitioning into the central nervous system (CNS), whereas (−)-cocaine has a plasma half-life of approximately 45-90 minutes (for a relatively low dose of cocaine), long enough for manifestation of the CNS effects which peak in minutes. Under the overdose condition, BChE is saturated with (−)-cocaine and, thus, the plasma half-life of (−)-cocaine will be longer. Hence, BChE mutants with high activity against (−)-cocaine are highly desired for use in humans. Although some BChE mutants with increased catalytic activity over wild-type BChE have previously been generated, there exists a need for mutant BChE with even higher catalytic activity.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently-disclosed subject matter includes butyrylcholinesterase (BChE) polypeptide variants. In some embodiments the amino acid sequence of the BChE polypeptide variant includes an amino acid sequence selected from the group consisting of: SEQ ID NOS: 2, 4, 6, 8, 10, 12, 14, 16, 18, 20, 22, 24, 26, 28, 30, and 32, as set forth herein.

The presently-disclosed subject matter further includes a pharmaceutical composition that includes a butyrylcholinesterase polypeptide variant and a suitable pharmaceutical carrier.

The presently-disclosed subject matter further includes a method of treating a cocaine-induced condition, which includes administering to an individual an effective amount of BChE polypeptide variant or a pharmaceutical composition comprising a BChE polypeptide variant, as described herein, to lower blood cocaine concentration. In some embodiments, the BChE polypeptide variant exhibits a one-hundred-fold or more increase in cocaine hydrolysis catalytic efficiency compared to wild-type butyrylcholinesterase.

BRIEF DESCRIPTION OF THE SEQUENCE LISTING

SEQ ID NO: 1 is a nucleotide sequence encoding a butyrylcholinesterase (BChE) polypeptide variant of SEQ ID NO: 2;

SEQ ID NO: 2 is an amino acid sequence encoding a BChE polypeptide variant having the following amino acid substitutions, as compared to wild type BChE: A199S, F227A, P285A, S287G, A328W, and Y332G;

SEQ ID NO: 3 is a nucleotide sequence encoding a butyrylcholinesterase (BChE) polypeptide variant of SEQ ID NO: 4;

SEQ ID NO: 4 is an amino acid sequence encoding a BChE polypeptide variant having the following amino acid substitutions, as compared to wild type BChE: A199S, F227A, P285S, S287G, A328W, and Y332G;

SEQ ID NO: 5 is a nucleotide sequence encoding a butyrylcholinesterase (BChE) polypeptide variant of SEQ ID NO: 6;

SEQ ID NO: 6 is an amino acid sequence encoding a BChE polypeptide variant having the following amino acid substitutions, as compared to wild type BChE: A199S, F227A, P285Q, S287G, A328W, and Y332G;

SEQ ID NO: 7 is a nucleotide sequence encoding a butyrylcholinesterase (BChE) polypeptide variant of SEQ ID NO: 8;

SEQ ID NO: 8 is an amino acid sequence encoding a BChE polypeptide variant having the following amino acid substitutions, as compared to wild type BChE: A199S, F227P, S287G, A328W, and Y332G.

SEQ ID NO: 9 is a nucleotide sequence encoding a butyrylcholinesterase (BChE) polypeptide variant of SEQ ID NO: 10;

SEQ ID NO: 10 is an amino acid sequence encoding a BChE polypeptide variant having the following amino acid substitutions, as compared to wild type BChE: A199S, F227A, P285G, S287G, A328W, and Y332G;

SEQ ID NO: 11 is a nucleotide sequence encoding a butyrylcholinesterase (BChE) polypeptide variant of SEQ ID NO: 12;

SEQ ID NO: 12 is an amino acid sequence encoding a BChE polypeptide variant having the following amino acid substitutions, as compared to wild type BChE: A199S, F227A, L286M, S287G, A328W, and Y332G;

SEQ ID NO: 13 is a nucleotide sequence encoding a butyrylcholinesterase (BChE) polypeptide variant of SEQ ID NO: 14;

SEQ ID NO: 14 is an amino acid sequence encoding a BChE polypeptide variant having the following amino acid substitutions, as compared to wild type BChE: A199S, P285Q, S287G, A328W, and Y332G;

SEQ ID NO: 15 is a nucleotide sequence encoding a butyrylcholinesterase (BChE) polypeptide variant of SEQ ID NO: 16;

SEQ ID NO: 16 is an amino acid sequence encoding a BChE polypeptide variant having the following amino acid substitutions, as compared to wild type BChE: A199S, P285I, S287G, A328W, and Y332G;

SEQ ID NO: 17 is a nucleotide sequence encoding a butyrylcholinesterase (BChE) polypeptide variant of SEQ ID NO: 18;

SEQ ID NO: 18 is an amino acid sequence encoding a BChE polypeptide variant having the following amino acid substitutions, as compared to wild type BChE: A199S, F227G, S287G, A328W, and Y332G;

SEQ ID NO: 19 is a nucleotide sequence encoding a butyrylcholinesterase (BChE) polypeptide variant of SEQ ID NO: 20;

SEQ ID NO: 20 is an amino acid sequence encoding a BChE polypeptide variant having the following amino acid substitutions, as compared to wild type BChE: A199S, P285S, S287G, A328W, and Y332G;

SEQ ID NO: 21 is a nucleotide sequence encoding a butyrylcholinesterase (BChE) polypeptide variant of SEQ ID NO: 22;

SEQ ID NO: 22 is an amino acid sequence encoding a BChE polypeptide variant having the following amino acid substitutions, as compared to wild type BChE: A199S, F227V, S287G, A328W, and Y332G;

SEQ ID NO: 23 is a nucleotide sequence encoding a butyrylcholinesterase (BChE) polypeptide variant of SEQ ID NO: 24;

SEQ ID NO: 24 is an amino acid sequence encoding a BChE polypeptide variant having the following amino acid substitutions, as compared to wild type BChE: A199S, P285G, S287G, A328W, and Y332G;

SEQ ID NO: 25 is a nucleotide sequence encoding a butyrylcholinesterase (BChE) polypeptide variant of SEQ ID NO: 26;

SEQ ID NO: 26 is an amino acid sequence encoding a BChE polypeptide variant having the following amino acid substitutions, as compared to wild type BChE: A199S, F227I, S287G, A328W, and Y332G;

SEQ ID NO: 27 is a nucleotide sequence encoding a butyrylcholinesterase (BChE) polypeptide variant of SEQ ID NO: 28;

SEQ ID NO: 28 is an amino acid sequence encoding a BChE polypeptide variant having the following amino acid substitutions, as compared to wild type BChE: A199S, F227L, S287G, A328W, and Y332G;

SEQ ID NO: 29 is a nucleotide sequence encoding a butyrylcholinesterase (BChE) polypeptide variant of SEQ ID NO: 30;

SEQ ID NO: 30 is an amino acid sequence encoding a BChE polypeptide variant having the following amino acid substitutions, as compared to wild type BChE: A199S, L286M, S287G, A328W, and Y332G;

SEQ ID NO: 31 is a nucleotide sequence encoding a butyrylcholinesterase (BChE) polypeptide variant of SEQ ID NO: 32; and SEQ ID NO: 32 is an amino acid sequence encoding a BChE polypeptide variant having the following amino acid substitutions, as compared to wild type BChE: A199S, F227A, P285K, S287G, A328W, and Y332G.

standing and no unnecessary limitations are to be understood therefrom. In case of conflict, the specification of this document, including definitions, will control.

The presently-disclosed subject matter includes butyrylcholinesterase (BChE) polypeptide variants. The BChE polypeptide variants disclosed herein each have enhanced catalytic efficiency for (−)-cocaine, as compared to wild-type BChE. The presently-disclosed subject matter further includes a pharmaceutical composition including a butyrylcholinesterase polypeptide variant, as described herein, and a suitable pharmaceutical carrier. The presently-disclosed subject matter further includes a method of treating a cocaine-induced condition comprising administering to an individual an effective amount of a butyrylcholinesterase polypeptide variant, as disclosed herein, to lower blood cocaine concentration.

In some embodiments, the BChE polypeptide variant is selected from a BChE polypeptide variants set forth in Table 1. Table 1 also includes the SEQ ID NOs associated with the identified BChE polypeptide variants, as well as a summary of the approximate fold increase in catalytic efficiency against (−)-cocaine for the identified BChE polypeptide variants, as compared to wild type BChE.

TABLE 1

BChE Polypeptide Variants and Associated SEQ ID NOs

| Variant Number | Amino Acid Substitution | | | | | | | Catalytic Efficiency ($k_{cat}/K_M$) against (−)-cocaine (Approximate Fold Increase)[a] | Nucleic Acid SEQ ID NO: | Amino Acid SEQ ID NO: |
|---|---|---|---|---|---|---|---|---|---|---|
| | 199 | 227 | 285 | 286 | 287 | 328 | 332 | | | |
| 1 | A199S | F227A | P285A | — | S287G | A328W | Y332G | 4080 | 1 | 2 |
| 2 | A199S | F227A | P285S | — | S287G | A328W | Y332G | 3700 | 3 | 4 |
| 3 | A199S | F227A | P285Q | — | S287Q | A328W | Y332G | 3590 | 5 | 6 |
| 4 | A199S | F227P | — | — | S287G | A328W | Y332G | 1860 | 7 | 8 |
| 5 | A199S | F227A | P285G | — | S287G | A328W | Y332G | 2420 | 9 | 10 |
| 6 | A199S | F227A | — | L286M | S287G | A328W | Y332G | 2120 | 11 | 12 |
| 7 | A199S | — | P285Q | — | S287G | A328W | Y332G | 2220 | 13 | 14 |
| 8 | A199S | — | P285I | — | S287G | A328W | Y332G | 830 | 15 | 16 |
| 9 | A199S | F227G | — | — | S287G | A328W | Y332G | 2010 | 17 | 18 |
| 10 | A199S | — | P285S | — | S287G | A328W | Y332G | 1240 | 19 | 20 |
| 11 | A199S | F227V | — | — | S287G | A328W | Y332G | 950 | 21 | 22 |
| 12 | A199S | — | P285G | — | S287G | A328W | Y332G | 1250 | 23 | 24 |
| 13 | A199S | F227I | — | — | S287G | A328W | Y332G | 1240 | 25 | 26 |
| 14 | A199S | F227L | — | — | S287G | A328W | Y332G | 1100 | 27 | 28 |
| 15 | A199S | — | — | L286M | S287G | A328W | Y332G | 740 | 29 | 30 |
| 16 | A199S | F227A | P285K | — | S287G | A328W | Y332G | 1540 | 31 | 32 |

[a]The approximate ratio of the $k_{cat}/K_M$ value for the BChE mutant to that for the wild-type BChE against (−)-cocaine.

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood The terms "polypeptide", "protein", and "peptide", which are used interchangeably herein, refer to a polymer of the protein amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides, and proteins, unless otherwise noted. The terms "protein", "polypeptide", and "peptide" are used interchangeably herein when referring to a gene product. Thus, exemplary polypeptides include gene products, naturally occurring proteins, homologs, orthologs, paralogs, fragments and other equivalents, variants, and analogs of the foregoing.

The term "variant" refers to an amino acid sequence that is different from the reference polypeptide by one or more amino acids, e.g., one or more amino acid substitutions. For example a butyrylcholinesterase (BChE) polypeptide variant differs from wild-type BChE by one or more amino acid substitutions, i.e., mutations.

The terms "polypeptide fragment" or "fragment", when used in reference to a reference polypeptide, refers to a polypeptide in which amino acid residues are deleted as compared to the reference polypeptide itself, but where the remaining amino acid sequence is usually identical to the corresponding positions in the reference polypeptide. Such deletions can occur at the amino-terminus, carboxy-terminus of the reference polypeptide, or alternatively both. A fragment can also be a "functional fragment," in which case the fragment retains some or all of the activity of the reference polypeptide as described herein. For example, a functional fragment of a particular BChE polypeptide variant retains some or all of the cocaine hydrolysis activity, i.e., the catalytic efficiency for (−)-cocaine, of the particular BChE polypeptide variant. In this regard, the term "BChE polypeptide variant" is inclusive of functional fragments of the BChE polypeptide variant. Such fragments are typically are at least about 300, 325, 350, 375, 400, 425, 450, 475, 500, 525, or 550 amino acids long. One or more residues from about 1 to 67 and/or one or more residues from about 443 to 574 can be removed without substantially affecting the catalytic activity of the BChE polypeptide variant. As such, the term "BChE polypeptide variant" is inclusive of functional fragments wherein one or more residues from 1 to 67 and/or one or more residues from 443 to 574 is truncated relative to the full-length BChE polypeptide variant.

The BChE polypeptide variant (e.g., SEQ ID NOS: 2, 4, 6, 8, 10, 12, 14, 16, 18, 20, 22, 24, 26, 28, 30, and 32) can be formulated in a pharmaceutical composition along with a suitable pharmaceutical carrier known to one skilled in the art.

The present BChE variant polypeptides can be used in treating a cocaine-induced condition by administering to an individual, an effective amount of a BChE variant polypeptides, (e.g., SEQ ID NOS: 2, 4, 6, 8, 10, 12, 14, 16, 18, 20, 22, 24, 26, 28, 30, and 32), to lower blood cocaine concentration. The BChE polypeptide variant can be administered in the form of a pharmaceutical composition in which the BChE polypeptide variant is included with a suitable pharmaceutical carrier. Treatment of a cocaine-induced condition using one of the aforementioned BChE polypeptide variants can be in a manner that will be understood by those skilled in the art.

The preferred dose for administration of a BChE polypeptide variant or pharmaceutical composition in accordance with the presently-described subject matter is that amount which will be effective in lowering (−)-cocaine concentration in a patient's bloodstream, and one would readily recognize that this amount will vary greatly depending on the nature of cocaine consumed, e.g., injected or inhaled, and the condition of a patient. An "effective amount" of butyrylcholinesterase polypeptide variant or pharmaceutical composition to be used in accordance with the presently-disclosed subject matter is intended to mean a nontoxic but sufficient amount of the agent, such that the desired prophylactic or therapeutic effect is produced. Thus, the exact amount of the enzyme or a particular agent that is required will vary from subject to subject, depending on the species, age, and general condition of the subject, the severity of the condition being treated, the particular carrier or adjuvant being used and its mode of administration, and the like. Similarly, the dosing regimen should also be adjusted to suit the individual to whom the composition is administered and will once again vary with age, weight, metabolism, etc. of the individual. Accordingly, the "effective amount" of any particular butyrylcholinesterase polypeptide variant, or pharmaceutical composition thereof, will vary based on the particular circumstances, and an appropriate effective amount may be determined in each case of application by one of ordinary skill in the art using only routine experimentation.

The presently-disclosed subject matter is further illustrated by the following specific but non-limiting examples. The following examples may include compilations of data that are representative of data gathered at various times during the course of development and experimentation related to the presently-disclosed subject matter.

EXAMPLES

Embodiments of the BChE polypeptide variants of the presently-disclosed subject matter were made and studied using the following experimental procedure.

Site-directed mutagenesis of human BChE cDNA was performed by the QuikChange method of Braman, J.; Papworth, C.; Greener, A. *Methods Mol. Biol.* 1996, 57, 5731, incorporated herein by this reference. Mutations were generated from wild-type human BChE in a pRc/CMV expression plasmid in accordance with Xie, W.; Altamirano, C. V.; Bartels, C. F.; Speirs, R. J.; Cashman, J. R.; Lockridge, O. *Mol. Pharmacol.* 1999, 55, 83, each of which is incorporated herein by this reference. The expression plasmid pRc/CMV was kindly provided by Dr. O. Lockridge, University of Nebraska Medical Center (Omaha, Nebr.).

Using plasmid DNA as template and primers with specific base-pair alterations, mutations were made by polymerase chain reaction with Pfu DNA polymerase, for replication fidelity. The PCR product was treated with Dpn I endonuclease to digest the parental DNA template. Cloned pfu DNA polymerase and Dpn I endonuclease were obtained from Stratagene (La Jolla, Calif.). Modified plasmid DNA was transformed into *Escherichia coli*, amplified, and purified. The DNA sequences of the mutants were confirmed by DNA sequencing. All oligonucleotides were synthesized by the Integrated DNA Technologies, Inc. The QIAprep Spin Plasmid Miniprep Kit and Qiagen plasmid purification kit and QIAquick PCR purification kit were obtained from Qiagen (Santa Clarita, Calif.).

BChE mutants were expressed in human embryonic kidney cell line 293T/17. Cells were grown to 80-90% confluence in 6-well dishes and then transfected by Lipofectamine 2000 complexes of 4 ng plasmid DNA per each well. Cells were incubated at 37° C. in a $CO_2$ incubator for 24 hours and cells were moved to 60-mm culture vessel and cultured for four more days. The culture medium [10% fetal bovine serum in Dulbecco's modified Eagle's medium (DMEM)] was harvested for a BChE activity assay.

Human embryonic kidney 293T/17 cells were from ATCC (Manassas, Va.). Dulbecco's modified Eagle's medium (DMEM) was purchased from Fisher Scientific (Fairlawn, N.J.). Oligonucleotide primers were synthesized by the Integrated DNA Technologies and Analysis Facility of the University of Kentucky. 3,3',5,5'-Tetramethylbenzidine (TMB) was obtained from Sigma (Saint Louis, Mo.). Anti-butyrylcholinesterase (mouse monoclonal antibody, Product # HAH002-01) was purchased from AntibodyShop (Gentofte, Denmark) and Goat anti-mouse IgG HRP conjugate from Zymed (San Francisco, Calif.).

To measure cocaine and benzoic acid, the product of cocaine hydrolysis by BChE, sensitive radiometric assays based on toluene extraction of [$^3$H]-(−)-cocaine labeled on its benzene ring were used in accordance with Zheng, F.; Yang, W.; Ko, M.-C.; Liu, J.; Cho, H.; Gao, D.; Tong, M.; Tai, H.-H.; Woods, J. H.; Zhan, C.-G. "Most Efficient Cocaine Hydrolase Designed by Virtual Screening of Transition States", *J. Am. Chem. Soc.* 2008, 130, 12148-12155, which is incorporated herein by this reference. $^3$H-(−)-cocaine (50 Ci/mmol) was purchased from PerkinElmer Life Sciences (Boston, Mass.).

In brief, to initiate reactions, 100 nCi of [$^3$H]-(−)-cocaine was mixed with 100 μl of culture medium. Reactions proceeded at room temperature (25° C.) with varying concentrations of (−)-cocaine. Reactions were stopped by adding 300 μl of 0.02 M HCl, which neutralized the liberated benzoic acid while ensuring a positive charge on the residual cocaine. [$^3$H]benzoic acid was extracted by 1 ml of toluene and measured by scintillation counting. Finally, the measured (−)-cocaine concentration-dependent radiometric data were analyzed by using the standard Michaelis-Menten kinetics so that the catalytic efficiency ($k_{cat}/K_M$) was determined, along with the use of an enzyme-linked immunosorbent assay (ELISA) described in by Zheng, F.; Yang, W.; Ko, M.-C.; Liu, J.; Cho, H.; Gao, D.; Tong, M.; Tai, H.-H.; Woods, J. H.; Zhan, C.-G. "Most Efficient Cocaine Hydrolase Designed by Virtual Screening of Transition States", *J. Am. Chem. Soc.* 2008, 130, 12148-12155.

The catalytic efficiency ($k_{cat}/K_M$) of the BChE polypeptide variants of SEQ ID NO: 2, 4, 6, 8, 10, 12, 14, 16, 18, 20, 22, 24, 26, 28, 30, and 32 are set forth in Table 2.

TABLE 2

Catalytic Efficiency ($k_{cat}/K_M$) of BChE Polypeptide Variants

| Variant Number | Amino Acid SEQ ID NO: | Catalytic Efficiency against (−)-cocaine ($M^{-1}$ $min^{-1}$) | Catalytic Efficiency against (−)-cocaine (Approximate Fold Increase)[a] |
|---|---|---|---|
| 1 | 2 | 3.72 × 10$^9$ | 4080 |
| 2 | 4 | 3.37 × 10$^9$ | 3700 |
| 3 | 6 | 3.27 × 10$^9$ | 3590 |
| 4 | 8 | 1.69 × 10$^9$ | 1860 |
| 5 | 10 | 2.20 × 10$^9$ | 2420 |
| 6 | 12 | 1.93 × 10$^9$ | 2120 |
| 7 | 14 | 2.02 × 10$^9$ | 2220 |
| 8 | 16 | 7.56 × 10$^8$ | 830 |
| 9 | 18 | 1.83 × 10$^9$ | 2010 |
| 10 | 20 | 1.13 × 10$^9$ | 1240 |
| 11 | 22 | 8.65 × 10$^8$ | 950 |
| 12 | 24 | 1.14 × 10$^9$ | 1250 |
| 13 | 26 | 1.13 × 10$^9$ | 1240 |
| 14 | 28 | 1.00 × 10$^9$ | 1100 |
| 15 | 30 | 6.74 × 10$^8$ | 740 |
| 16 | 32 | 1.40 × 10$^9$ | 1540 |

[a]The approximate ratio of the $k_{cat}/K_M$ value for the BChE mutant to that for the wild-type BChE against (−)-cocaine.

The catalytic efficiencies ($k_{cat}/K_M$) of the BChE polypeptide variants were found to be between about 6.74×10$^8$ and 3.72×10$^9$ $M^{-1}$ $min^{-1}$, which is about 740 to about 4080 times the $k_{cat}/K_M$ value (9.11×10$^5$ $M^{-1}$ $min^{-1}$) of the wild-type BChE.

Enzyme-linked immunosorbent assays (ELISA) were preformed as follows. The ELISA buffers used were the same as those described in the literature such as Brock, A.; Mortensen, V.; Loft, A. G. R.; Nergaard-Pedersen, B. *J. Clin. Chem. Clin. Biochem.* 1990, 28, 221-224; and Khattab, A. D.; Walker, C. H.; Johnston, G.; Siddiqui, M. K. Saphier, P. W. *Environmental Toxicology and Chemistry* 1994, 13, 1661-1667, both of which are incorporated herein by this reference. The coating buffer was 0.1 M sodium carbonate/bicarbonate buffer, pH 9.5. The diluent buffer (EIA buffer) was potassium phosphate monobasic/potassium phosphate monohydrate buffer, pH 7.5, containing 0.9% sodium chloride and 0.1% bovine serum albumin. The washing buffer (PBS-T) was 0.01 M potassium phosphate monobasic/potassium phosphate monohydrate buffer, pH 7.5, containing 0.05% (v/v) Tween-20. All the assays were performed in triplicate. Each well of an ELISA microtiter plate was filled with 100 μl of the mixture buffer consisting of 20 μl culture medium and 80 μl coating buffer. The plate was covered and incubated overnight at 4° C. to allow the antigen to bind to the plate. The solutions were then removed and the wells were washed four times with PBS-T. The washed wells were filled with 200 μl diluent buffer and kept shaking for 1.5 h at room temperature (25° C.). After washing with PBS-T for four times, the wells were filled with 100 μl antibody (1:8000) and were incubated for 1.5 h, followed by washing for four times. Then, the wells were filled with 100 μl goat anti-mouse IgG HRP conjugate complex diluted to a final 1:3000 dilution, and were incubated at room temperature for 1.5 h, followed by washing for four times. The enzyme reactions were started by addition of 100 μl substrate (TMB) solution. The reactions were stopped after 15 min by the addition of 100 μl of 2 M sulfuric acid, and the absorbance was read at 460 nm using a Bio-Rad ELISA plate reader.

While the terms used herein are believed to be well understood by one of ordinary skill in the art, the definitions set forth herein are provided to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±50%, in some embodiments ±40%, in some embodiments ±30%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

Throughout this document, various references are mentioned. All such references are incorporated herein by reference.

What is claimed is:

1. A butyrylcholinesterase polypeptide variant comprising the amino acid sequence of SEQ ID NO: 2.

2. A pharmaceutical composition comprising a butyrylcholinesterase polypeptide variant comprising the amino acid sequence of SEQ ID NO: 2 and a suitable pharmaceutical carrier.

3. A method of treating a cocaine-induced condition comprising administering to an individual an effective amount of a butyrylcholinesterase polypeptide variant of claim 1 to lower blood cocaine concentration.

4. The method of claim 3, wherein said butyrylcholinesterase polypeptide variant exhibits a one-hundred-fold or more increase in cocaine hydrolysis catalytic efficiency compared to butyrylcholinesterase.

5. A method of treating a cocaine-induced condition comprising administering to an individual an effective amount of the pharmaceutical composition of claim 2 to lower blood cocaine concentration.

* * * * *

SEQUENCE LISTING

<160> NUMBER OF SEQ ID NOS: 32

<210> SEQ ID NO 1
<211> LENGTH: 1722
<212> TYPE: DNA
<213> ORGANISM: Artificial Sequence
<220> FEATURE:
<223> OTHER INFORMATION: mutant of human BChE

<400> SEQUENCE: 1

```
gaagatgaca tcataattgc aacaaagaat ggaaaagtca gagggatgaa cttgacagtt      60
tttggtggca cggtaacagc cttttcttgga attccctatg cacagccacc tcttggtaga   120
cttcgattca aaaagccaca gtctctgacc aagtggtctg atatttggaa tgccacaaaa   180
tatgcaaatt cttgctgtca gaacatagat caaagttttc caggcttcca tggatcagag   240
atgtggaacc caaacactga cctcagtgaa gactgtttat atctaaatgt atggattcca   300
gcacctaaac caaaaaatgc cactgtattg atatggattt atggtggtgg ttttcaaact   360
ggaacatcat ctttacatgt ttatgatggc aagtttctgg ctcgggttga aagagttatt   420
gtagtgtcaa tgaactatag ggtgggtgcc ctaggattct tagctttgcc aggaaatcct   480
gaggctccag ggaacatggg tttatttgat aacagttgg ctcttcagtg ggttcaaaaa    540
aatatagcag cctttggtgg aaatcctaaa agtgtaactc tctttggaga aagttccgga   600
gcagcttcag ttagcctgca tttgctttct cctggaagcc attcattgtt caccagagcc   660
attctgcaaa gtggttccgc taatgctcct tgggcggtaa catctcttta tgaagctagg   720
aacagaacgt tgaacttagc taaattgact ggttgctcta gagagaatga gactgaaata   780
atcaagtgtc ttagaaataa agatccccaa gaaattcttc tgaatgaagc atttgttgtc   840
ccctatggga ctgctttggg tgtaaacttt ggtccgaccg tggatggtga tttctctcact   900
gacatgccag acatattact tgaacttgga caatttaaaa aaacccagat tttggtgggt   960
gttaataaag atgaagggac atggttttta gtcggtggtg ctcctggctt cagcaaagat  1020
aacaatagta tcataactag aaaagaattt caggaaggtt taaaaatatt ttttccagga  1080
gtgagtgagt ttgaaaagga atccatcctt tttcattaca cagactgggt agatgatcag  1140
agacctgaaa actaccgtga ggcctttggg gatgttgttg gggattataa tttcatatgc  1200
cctgccttgg agttcaccaa gaagttctca gaatggggaa ataatgcctt tttctactat  1260
tttgaacacc gatcctccaa acttccgtgg ccagaatgga tgggagtgat gcatggctat  1320
gaaattgaat tgtctttgg tttacctctg gaaagaagag ataattacac aaaagccgag  1380
gaaatttga gtagatccat agtgaaacgg tgggcaaatt ttgcaaaata tgggaatcca  1440
aatgagactc agaacaatag cacaagctgg cctgtcttca aaagcactga acaaaaatat  1500
ctaaccttga atacagagtc aacaagaata atgacgaaac tacgtgctca acaatgtcga  1560
ttctggacat catttttttcc aaaagtcttg gaaatgacag gaaatattga tgaagcagaa  1620
tgggagtgga agcaggatt ccatcgctgg aacaattaca tgatggactg gaaaaatcaa  1680
tttaacgatt acactagcaa gaaagaaagt tgtgtgggtc tc                    1722
```

<210> SEQ ID NO 2
<211> LENGTH: 574
<212> TYPE: PRT
<213> ORGANISM: Artificial Sequence
<220> FEATURE:
<223> OTHER INFORMATION: mutant of human BChE

<400> SEQUENCE: 2

```
Glu Asp Asp Ile Ile Ile Ala Thr Lys Asn Gly Lys Val Arg Gly Met
1               5                   10                  15

Asn Leu Thr Val Phe Gly Gly Thr Val Thr Ala Phe Leu Gly Ile Pro
            20                  25                  30

Tyr Ala Gln Pro Pro Leu Gly Arg Leu Arg Phe Lys Lys Pro Gln Ser
        35                  40                  45

Leu Thr Lys Trp Ser Asp Ile Trp Asn Ala Thr Lys Tyr Ala Asn Ser
    50                  55                  60

Cys Cys Gln Asn Ile Asp Gln Ser Phe Pro Gly Phe His Gly Ser Glu
65                  70                  75                  80

Met Trp Asn Pro Asn Thr Asp Leu Ser Glu Asp Cys Leu Tyr Leu Asn
                85                  90                  95

Val Trp Ile Pro Ala Pro Lys Pro Lys Asn Ala Thr Val Leu Ile Trp
            100                 105                 110

Ile Tyr Gly Gly Gly Phe Gln Thr Gly Thr Ser Ser Leu His Val Tyr
        115                 120                 125

Asp Gly Lys Phe Leu Ala Arg Val Glu Arg Val Ile Val Val Ser Met
    130                 135                 140

Asn Tyr Arg Val Gly Ala Leu Gly Phe Leu Ala Leu Pro Gly Asn Pro
145                 150                 155                 160

Glu Ala Pro Gly Asn Met Gly Leu Phe Asp Gln Gln Leu Ala Leu Gln
                165                 170                 175

Trp Val Gln Lys Asn Ile Ala Ala Phe Gly Gly Asn Pro Lys Ser Val
            180                 185                 190

Thr Leu Phe Gly Glu Ser Ser Gly Ala Ala Ser Val Ser Leu His Leu
        195                 200                 205

Leu Ser Pro Gly Ser His Ser Leu Phe Thr Arg Ala Ile Leu Gln Ser
    210                 215                 220

Gly Ser Ala Asn Ala Pro Trp Ala Val Thr Ser Leu Tyr Glu Ala Arg
225                 230                 235                 240

Asn Arg Thr Leu Asn Leu Ala Lys Leu Thr Gly Cys Ser Arg Glu Asn
                245                 250                 255

Glu Thr Glu Ile Ile Lys Cys Leu Arg Asn Lys Asp Pro Gln Glu Ile
            260                 265                 270

Leu Leu Asn Glu Ala Phe Val Val Pro Tyr Gly Thr Ala Leu Gly Val
        275                 280                 285

Asn Phe Gly Pro Thr Val Asp Gly Asp Phe Leu Thr Asp Met Pro Asp
    290                 295                 300

Ile Leu Leu Glu Leu Gly Gln Phe Lys Lys Thr Gln Ile Leu Val Gly
305                 310                 315                 320

Val Asn Lys Asp Glu Gly Thr Trp Phe Leu Val Gly Gly Ala Pro Gly
                325                 330                 335

Phe Ser Lys Asp Asn Asn Ser Ile Ile Thr Arg Lys Glu Phe Gln Glu
            340                 345                 350

Gly Leu Lys Ile Phe Phe Pro Gly Val Ser Glu Phe Gly Lys Glu Ser
        355                 360                 365

Ile Leu Phe His Tyr Thr Asp Trp Val Asp Asp Gln Arg Pro Glu Asn
    370                 375                 380

Tyr Arg Glu Ala Leu Gly Asp Val Val Gly Asp Tyr Asn Phe Ile Cys
385                 390                 395                 400

Pro Ala Leu Glu Phe Thr Lys Lys Phe Ser Glu Trp Gly Asn Asn Ala
```

```
                405                 410                 415
Phe Phe Tyr Tyr Phe Glu His Arg Ser Ser Lys Leu Pro Trp Pro Glu
            420                 425                 430

Trp Met Gly Val Met His Gly Tyr Glu Ile Glu Phe Val Phe Gly Leu
        435                 440                 445

Pro Leu Glu Arg Arg Asp Asn Tyr Thr Lys Ala Glu Glu Ile Leu Ser
    450                 455                 460

Arg Ser Ile Val Lys Arg Trp Ala Asn Phe Ala Lys Tyr Gly Asn Pro
465                 470                 475                 480

Asn Glu Thr Gln Asn Asn Ser Thr Ser Trp Pro Val Phe Lys Ser Thr
                485                 490                 495

Glu Gln Lys Tyr Leu Thr Leu Asn Thr Glu Ser Thr Arg Ile Met Thr
            500                 505                 510

Lys Leu Arg Ala Gln Gln Cys Arg Phe Trp Thr Ser Phe Phe Pro Lys
        515                 520                 525

Val Leu Glu Met Thr Gly Asn Ile Asp Glu Ala Glu Trp Glu Trp Lys
    530                 535                 540

Ala Gly Phe His Arg Trp Asn Asn Tyr Met Met Asp Trp Lys Asn Gln
545                 550                 555                 560

Phe Asn Asp Tyr Thr Ser Lys Lys Glu Ser Cys Val Gly Leu
                565                 570

<210> SEQ ID NO 3
<211> LENGTH: 1722
<212> TYPE: DNA
<213> ORGANISM: Artificial Sequence
<220> FEATURE:
<223> OTHER INFORMATION: mutant of human BChE

<400> SEQUENCE: 3
gaagatgaca tcataattgc aacaaagaat ggaaaagtca gagggatgaa cttgacagtt      60
tttggtggca cggtaacagc ctttcttgga attccctatg cacagccacc tcttggtaga     120
cttcgattca aaaagccaca gtctctgacc aagtggtctg atatttggaa tgccacaaaa     180
tatgcaaatt cttgctgtca gaacatagat caaagttttc caggcttcca tggatcagag     240
atgtggaacc caaacactga cctcagtgaa gactgtttat atctaaatgt atggattcca     300
gcacctaaac caaaaaatgc cactgtattg atatggattt atggtggtgg ttttcaaact     360
ggaacatcat ctttacatgt ttatgatggc aagtttctgg ctcgggttga aagagttatt     420
gtagtgtcaa tgaactatag ggtgggtgcc ctaggattcc tagctttgcc aggaaatcct     480
gaggctccag ggaacatggg tttatttgat caacagttgg ctcttcagtg ggttcaaaaa     540
aatatagcag cctttggtgg aaatcctaaa agtgtaactc tctttggaga aagttccgga     600
gcagcttcag ttagcctgca tttgctttct cctggaagcc attcattgtt caccagagcc     660
attctgcaaa gtggttccgc taatgctcct tgggcggtaa catctcttta tgaagctagg     720
aacagaacgt tgaacttagc taaattgact ggttgctcta gagagaatga gactgaaata     780
atcaagtgtc ttagaaataa agatccccaa gaaattcttc tgaatgaagc atttgttgtc     840
ccctatggga cttccttggg tgtaaacttt ggtccgaccg tggatggtga ttttctcact     900
gacatgccag acatattact tgaacttgga caatttaaaa aaacccagat ttggtgggt      960
gttaataaag atgaagggac atggtttta gtcggtggtg ctcctggctt cagcaaagat    1020
aacaatagta tcataactag aaaagaattt caggaaggtt aaaaatatt ttttccagga    1080
gtgagtgagt ttggaaagga atccatcctt tttcattaca cagactggt agatgatcag    1140
```

-continued

```
agacctgaaa actaccgtga ggccttgggt gatgttgttg gggattataa tttcatatgc    1200
cctgccttgg agttcaccaa gaagttctca gaatggggaa ataatgcctt tttctactat    1260
tttgaacacc gatcctccaa acttccgtgg ccagaatgga tgggagtgat gcatggctat    1320
gaaattgaat ttgtctttgg tttacctctg aaagaagag ataattacac aaaagccgag     1380
gaaattttga gtagatccat agtgaaacgg tgggcaaatt ttgcaaaata tgggaatcca    1440
aatgagactc agaacaatag cacaagctgg cctgtcttca aaagcactga acaaaaatat    1500
ctaaccttga atacagagtc aacaagaata atgacgaaac tacgtgctca acaatgtcga    1560
ttctggacat cattttttcc aaaagtcttg gaaatgacag gaaatattga tgaagcagaa    1620
tgggagtgga agcaggatt ccatcgctgg aacaattaca tgatggactg gaaaaatcaa     1680
tttaacgatt acactagcaa gaaagaaagt tgtgtgggtc tc                       1722
```

<210> SEQ ID NO 4
<211> LENGTH: 574
<212> TYPE: PRT
<213> ORGANISM: Artificial Sequence
<220> FEATURE:
<223> OTHER INFORMATION: mutant of human BChE

<400> SEQUENCE: 4

```
Glu Asp Asp Ile Ile Ile Ala Thr Lys Asn Gly Lys Val Arg Gly Met
1               5                   10                  15

Asn Leu Thr Val Phe Gly Gly Thr Val Thr Ala Phe Leu Gly Ile Pro
            20                  25                  30

Tyr Ala Gln Pro Pro Leu Gly Arg Leu Arg Phe Lys Lys Pro Gln Ser
        35                  40                  45

Leu Thr Lys Trp Ser Asp Ile Trp Asn Ala Thr Lys Tyr Ala Asn Ser
    50                  55                  60

Cys Cys Gln Asn Ile Asp Gln Ser Phe Pro Gly Phe His Gly Ser Glu
65                  70                  75                  80

Met Trp Asn Pro Asn Thr Asp Leu Ser Glu Asp Cys Leu Tyr Leu Asn
                85                  90                  95

Val Trp Ile Pro Ala Pro Lys Pro Lys Asn Ala Thr Val Leu Ile Trp
            100                 105                 110

Ile Tyr Gly Gly Gly Phe Gln Thr Gly Thr Ser Ser Leu His Val Tyr
        115                 120                 125

Asp Gly Lys Phe Leu Ala Arg Val Glu Arg Val Ile Val Val Ser Met
    130                 135                 140

Asn Tyr Arg Val Gly Ala Leu Gly Phe Leu Ala Leu Pro Gly Asn Pro
145                 150                 155                 160

Glu Ala Pro Gly Asn Met Gly Leu Phe Asp Gln Gln Leu Ala Leu Gln
                165                 170                 175

Trp Val Gln Lys Asn Ile Ala Ala Phe Gly Gly Asn Pro Lys Ser Val
            180                 185                 190

Thr Leu Phe Gly Glu Ser Ser Gly Ala Ala Ser Val Ser Leu His Leu
        195                 200                 205

Leu Ser Pro Gly Ser His Ser Leu Phe Thr Arg Ala Ile Leu Gln Ser
    210                 215                 220

Gly Ser Ala Asn Ala Pro Trp Ala Val Thr Ser Leu Tyr Glu Ala Arg
225                 230                 235                 240

Asn Arg Thr Leu Asn Leu Ala Lys Leu Thr Gly Cys Ser Arg Glu Asn
                245                 250                 255
```

| | | | | | | | | | | | | |
|---|---|---|---|---|---|---|---|---|---|---|---|---|
| Glu | Thr | Glu | Ile | Ile | Lys | Cys | Leu | Arg | Asn | Lys | Asp | Pro | Gln | Glu | Ile |
| | | 260 | | | | | 265 | | | | | 270 | | | |

Glu Thr Glu Ile Ile Lys Cys Leu Arg Asn Lys Asp Pro Gln Glu Ile
            260                 265                 270

Leu Leu Asn Glu Ala Phe Val Val Pro Tyr Gly Thr Ser Leu Gly Val
            275                 280                 285

Asn Phe Gly Pro Thr Val Asp Gly Asp Phe Leu Thr Asp Met Pro Asp
            290                 295                 300

Ile Leu Leu Glu Leu Gly Gln Phe Lys Lys Thr Gln Ile Leu Val Gly
305                 310                 315                 320

Val Asn Lys Asp Glu Gly Thr Trp Phe Leu Val Gly Gly Ala Pro Gly
            325                 330                 335

Phe Ser Lys Asp Asn Asn Ser Ile Ile Thr Arg Lys Glu Phe Gln Glu
            340                 345                 350

Gly Leu Lys Ile Phe Phe Pro Gly Val Ser Glu Phe Gly Lys Glu Ser
            355                 360                 365

Ile Leu Phe His Tyr Thr Asp Trp Val Asp Asp Gln Arg Pro Glu Asn
            370                 375                 380

Tyr Arg Glu Ala Leu Gly Asp Val Val Gly Asp Tyr Asn Phe Ile Cys
385                 390                 395                 400

Pro Ala Leu Glu Phe Thr Lys Lys Phe Ser Glu Trp Gly Asn Asn Ala
            405                 410                 415

Phe Phe Tyr Tyr Phe Glu His Arg Ser Ser Lys Leu Pro Trp Pro Glu
            420                 425                 430

Trp Met Gly Val Met His Gly Tyr Glu Ile Glu Phe Val Phe Gly Leu
            435                 440                 445

Pro Leu Glu Arg Arg Asp Asn Tyr Thr Lys Ala Glu Glu Ile Leu Ser
            450                 455                 460

Arg Ser Ile Val Lys Arg Trp Ala Asn Phe Ala Lys Tyr Gly Asn Pro
465                 470                 475                 480

Asn Glu Thr Gln Asn Asn Ser Thr Ser Trp Pro Val Phe Lys Ser Thr
            485                 490                 495

Glu Gln Lys Tyr Leu Thr Leu Asn Thr Glu Ser Thr Arg Ile Met Thr
            500                 505                 510

Lys Leu Arg Ala Gln Gln Cys Arg Phe Trp Thr Ser Phe Phe Pro Lys
            515                 520                 525

Val Leu Glu Met Thr Gly Asn Ile Asp Glu Ala Glu Trp Glu Trp Lys
            530                 535                 540

Ala Gly Phe His Arg Trp Asn Asn Tyr Met Met Asp Trp Lys Asn Gln
545                 550                 555                 560

Phe Asn Asp Tyr Thr Ser Lys Lys Glu Ser Cys Val Gly Leu
            565                 570

<210> SEQ ID NO 5
<211> LENGTH: 1722
<212> TYPE: DNA
<213> ORGANISM: Artificial Sequence
<220> FEATURE:
<223> OTHER INFORMATION: mutant of human BChE

<400> SEQUENCE: 5
gaagatgaca tcataattgc aacaaagaat ggaaaagtca gagggatgaa cttgacagtt      60
tttggtggca cggtaacagc ctttcttgga attccctatg cacagccacc tcttggtaga    120
cttcgattca aaaagccaca gtctctgacc aagtggtctg atatttggaa tgccacaaaa    180
tatgcaaatt cttgctgtca gaacatagat caaagttttc caggcttcca tggatcagag    240
atgtggaacc caaacactga cctcagtgaa gactgtttat atctaaatgt atggattcca    300

-continued

```
gcacctaaac caaaaaatgc cactgtattg atatggattt atggtggtgg ttttcaaact      360
ggaacatcat ctttacatgt ttatgatggc aagtttctgg ctcgggttga aagagttatt      420
gtagtgtcaa tgaactatag ggtgggtgcc ctaggattct tagctttgcc aggaaatcct      480
gaggctccag ggaacatggg tttatttgat caacagttgg ctcttcagtg ggttcaaaaa      540
aatatagcag cctttggtgg aaatcctaaa agtgtaactc tctttggaga aagttccgga      600
gcagcttcag ttagcctgca tttgctttct cctggaagcc attcattgtt caccagagcc      660
attctgcaaa gtggttccgc taatgctcct gggcggtaa catctcttta tgaagctagg       720
aacagaacgt tgaacttagc taaattgact ggttgctcta gagagaatga gactgaaata      780
atcaagtgtc ttagaaataa agatccccaa gaaattcttc tgaatgaagc atttgttgtc      840
ccctatggga ctcagttggg tgtaaacttt ggtccgaccg tggatggtga ttttctcact      900
gacatgccag acatattact tgaacttgga caatttaaaa aaacccagat tttggtgggt      960
gttaataaag atgaagggac atggttttta gtcggtggtg ctcctggctt cagcaaagat     1020
aacaatagta tcataactag aaaagaattt caggaaggtt taaaaatatt ttttccagga     1080
gtgagtgagt ttggaaagga atccatcctt tttcattaca cagactgggt agatgatcag     1140
agacctgaaa actaccgtga ggccttgggt gatgttgttg gggattataa tttcatatgc     1200
cctgccttgg agttcaccaa gaagttctca gaatggggaa ataatgcctt tttctactat     1260
tttgaacacc gatcctccaa acttccgtgg ccagaatgga tgggagtgat gcatggctat     1320
gaaattgaat ttgtctttgg tttacctctg aaagaagag ataattacac aaaagccgag      1380
gaaattttga gtagatccat agtgaaacgg tgggcaaatt ttgcaaaata tgggaatcca     1440
aatgagactc agaacaatag cacaagctgg cctgtcttca aaagcactga acaaaaatat     1500
ctaaccttga atacagagtc aacaagaata atgacgaaac tacgtgctca acaatgtcga     1560
ttctggacat cattttttcc aaaagtcttg gaaatgacag gaaatattga tgaagcagaa     1620
tgggagtgga agcaggatt ccatcgctgg aacaattaca tgatggactg gaaaaatcaa      1680
tttaacgatt acactagcaa gaaagaaagt tgtgtgggtc tc                        1722
```

<210> SEQ ID NO 6
<211> LENGTH: 574
<212> TYPE: PRT
<213> ORGANISM: Artificial Sequence
<220> FEATURE:
<223> OTHER INFORMATION: mutant of human BChE

<400> SEQUENCE: 6

```
Glu Asp Asp Ile Ile Ile Ala Thr Lys Asn Gly Lys Val Arg Gly Met
 1               5                  10                  15

Asn Leu Thr Val Phe Gly Gly Thr Val Thr Ala Phe Leu Gly Ile Pro
                20                  25                  30

Tyr Ala Gln Pro Pro Leu Gly Arg Leu Arg Phe Lys Lys Pro Gln Ser
            35                  40                  45

Leu Thr Lys Trp Ser Asp Ile Trp Asn Ala Thr Lys Tyr Ala Asn Ser
        50                  55                  60

Cys Cys Gln Asn Ile Asp Gln Ser Phe Pro Gly Phe His Gly Ser Glu
    65                  70                  75                  80

Met Trp Asn Pro Asn Thr Asp Leu Ser Glu Asp Cys Leu Tyr Leu Asn
                85                  90                  95

Val Trp Ile Pro Ala Pro Lys Pro Lys Asn Ala Thr Val Leu Ile Trp
            100                 105                 110
```

-continued

```
Ile Tyr Gly Gly Gly Phe Gln Thr Gly Thr Ser Ser Leu His Val Tyr
        115                 120                 125
Asp Gly Lys Phe Leu Ala Arg Val Glu Arg Val Ile Val Val Ser Met
130                 135                 140
Asn Tyr Arg Val Gly Ala Leu Gly Phe Leu Ala Leu Pro Gly Asn Pro
145                 150                 155                 160
Glu Ala Pro Gly Asn Met Gly Leu Phe Asp Gln Gln Leu Ala Leu Gln
                165                 170                 175
Trp Val Gln Lys Asn Ile Ala Ala Phe Gly Asn Pro Lys Ser Val
                180                 185                 190
Thr Leu Phe Gly Glu Ser Ser Gly Ala Ala Ser Val Ser Leu His Leu
        195                 200                 205
Leu Ser Pro Gly Ser His Ser Leu Phe Thr Arg Ala Ile Leu Gln Ser
        210                 215                 220
Gly Ser Ala Asn Ala Pro Trp Ala Val Thr Ser Leu Tyr Glu Ala Arg
225                 230                 235                 240
Asn Arg Thr Leu Asn Leu Ala Lys Leu Thr Gly Cys Ser Arg Glu Asn
                245                 250                 255
Glu Thr Glu Ile Ile Lys Cys Leu Arg Asn Lys Asp Pro Gln Glu Ile
                260                 265                 270
Leu Leu Asn Glu Ala Phe Val Val Pro Tyr Gly Thr Gln Leu Gly Val
        275                 280                 285
Asn Phe Gly Pro Thr Val Asp Gly Asp Phe Leu Thr Asp Met Pro Asp
        290                 295                 300
Ile Leu Leu Glu Leu Gly Gln Phe Lys Lys Thr Gln Ile Leu Val Gly
305                 310                 315                 320
Val Asn Lys Asp Glu Gly Thr Trp Phe Leu Val Gly Gly Ala Pro Gly
                325                 330                 335
Phe Ser Lys Asp Asn Asn Ser Ile Ile Thr Arg Lys Glu Phe Gln Glu
                340                 345                 350
Gly Leu Lys Ile Phe Phe Pro Gly Val Ser Glu Phe Gly Lys Glu Ser
        355                 360                 365
Ile Leu Phe His Tyr Thr Asp Trp Val Asp Asp Gln Arg Pro Glu Asn
        370                 375                 380
Tyr Arg Glu Ala Leu Gly Asp Val Val Gly Asp Tyr Asn Phe Ile Cys
385                 390                 395                 400
Pro Ala Leu Glu Phe Thr Lys Lys Phe Ser Glu Trp Gly Asn Asn Ala
                405                 410                 415
Phe Phe Tyr Tyr Phe Glu His Arg Ser Ser Lys Leu Pro Trp Pro Glu
                420                 425                 430
Trp Met Gly Val Met His Gly Tyr Glu Ile Glu Phe Val Phe Gly Leu
        435                 440                 445
Pro Leu Glu Arg Arg Asp Asn Tyr Thr Lys Ala Glu Glu Ile Leu Ser
        450                 455                 460
Arg Ser Ile Val Lys Arg Trp Ala Asn Phe Ala Lys Tyr Gly Asn Pro
465                 470                 475                 480
Asn Glu Thr Gln Asn Asn Ser Thr Ser Trp Pro Val Phe Lys Ser Thr
                485                 490                 495
Glu Gln Lys Tyr Leu Thr Leu Asn Thr Glu Ser Thr Arg Ile Met Thr
                500                 505                 510
Lys Leu Arg Ala Gln Gln Cys Arg Phe Trp Thr Ser Phe Phe Pro Lys
        515                 520                 525
```

```
Val Leu Glu Met Thr Gly Asn Ile Asp Glu Ala Glu Trp Glu Trp Lys
    530                 535                 540

Ala Gly Phe His Arg Trp Asn Asn Tyr Met Met Asp Trp Lys Asn Gln
545                 550                 555                 560

Phe Asn Asp Tyr Thr Ser Lys Lys Glu Ser Cys Val Gly Leu
                565                 570
```

<210> SEQ ID NO 7
<211> LENGTH: 1722
<212> TYPE: DNA
<213> ORGANISM: Artificial Sequence
<220> FEATURE:
<223> OTHER INFORMATION: mutant of human BChE

<400> SEQUENCE: 7

```
gaagatgaca tcataattgc aacaaagaat ggaaaagtca gagggatgaa cttgacagtt      60
tttggtggca cggtaacagc ctttcttgga attccctatg cacagccacc tcttggtaga     120
cttcgattca aaaagccaca gtctctgacc aagtggtctg atatttggaa tgccacaaaa     180
tatgcaaatt cttgctgtca gaacatagat caaagttttc caggcttcca tggatcagag     240
atgtggaacc caaacactga cctcagtgaa gactgtttat atctaaatgt atggattcca     300
gcacctaaac caaaaaatgc cactgtattg atatggattt atggtggtgg ttttcaaact     360
ggaacatcat ctttacatgt ttatgatggc aagtttctgg ctcgggttga aagagttatt     420
gtagtgtcaa tgaactatag ggtgggtgcc ctaggattct tagctttgcc aggaaatcct     480
gaggctccag ggaacatggg tttatttgat caacagttgg ctcttcagtg ggttcaaaaa     540
aatatagcag cctttggtgg aaatcctaaa agtgtaactc tctttggaga agttccggaa     600
gcagcttcag ttagcctgca tttgctttct cctggaagcc attcattgtt caccagagcc     660
attctgcaaa gtggttcccc gaatgctcct tgggcggtaa catctcttta tgaagctagg     720
aacagaacgt tgaacttagc taaattgact ggttgctcta gagagaatga gactgaaata     780
atcaagtgtc ttagaaataa agatcccaa gaaattcttc tgaatgaagc atttgttgtc     840
ccctatggga ctcctttggg tgtaaacttt ggtccgaccg tggatggtga ttttctcact     900
gacatgccag acatattact tgaacttgga caatttaaaa aacccagat tttggtgggt     960
gttaataaag atgaagggac atggtttta gtcggtggtg ctcctggctt cagcaaagat    1020
aacaatagta tcataactag aaaagaattt caggaaggtt taaaaatatt ttttccagga    1080
gtgagtgagt ttgaaaagga atccatcctt tttcattaca cagactgggt agatgatcag    1140
agacctgaaa actaccgtga ggccttgggt gatgttgttg gggattataa tttcatatgc    1200
cctgccttgg agttcaccaa gaagttctca gaatggggaa ataatgcctt tttctactat    1260
tttgaacacc gatcctccaa acttccgtgg ccagaatgga tgggagtgat gcatggctat    1320
gaaattgaat tgtctttgg tttacctctg gaaagaagag ataattacac aaaagccgag    1380
gaaattttga gtagatccat agtgaaacgg tgggcaaatt ttgcaaaata tgggaatcca    1440
aatgagactc agaacaatag cacaagctgg cctgtcttca aaagcactga acaaaaatat    1500
ctaaccttga atacagagtc aacaagaata atgacgaaac tacgtgctca acaatgtcga    1560
ttctggacat cattttttcc aaaagtcttg gaaatgacag gaaatattga tgaagcagaa    1620
tgggagtgga agcaggatt ccatcgctgg aacaattaca tgatggactg gaaaaatcaa    1680
tttaacgatt acactagcaa gaaagaaagt tgtgtgggtc tc                       1722
```

<210> SEQ ID NO 8

-continued

<211> LENGTH: 574
<212> TYPE: PRT
<213> ORGANISM: Artificial Sequence
<220> FEATURE:
<223> OTHER INFORMATION: mutant of human BChE

<400> SEQUENCE: 8

```
Glu Asp Asp Ile Ile Ile Ala Thr Lys Asn Gly Lys Val Arg Gly Met
1               5                   10                  15

Asn Leu Thr Val Phe Gly Gly Thr Val Thr Ala Phe Leu Gly Ile Pro
            20                  25                  30

Tyr Ala Gln Pro Pro Leu Gly Arg Leu Arg Phe Lys Lys Pro Gln Ser
        35                  40                  45

Leu Thr Lys Trp Ser Asp Ile Trp Asn Ala Thr Lys Tyr Ala Asn Ser
    50                  55                  60

Cys Cys Gln Asn Ile Asp Gln Ser Phe Pro Gly Phe His Gly Ser Glu
65                  70                  75                  80

Met Trp Asn Pro Asn Thr Asp Leu Ser Glu Asp Cys Leu Tyr Leu Asn
                85                  90                  95

Val Trp Ile Pro Ala Pro Lys Pro Lys Asn Ala Thr Val Leu Ile Trp
            100                 105                 110

Ile Tyr Gly Gly Gly Phe Gln Thr Gly Thr Ser Ser Leu His Val Tyr
        115                 120                 125

Asp Gly Lys Phe Leu Ala Arg Val Glu Arg Val Ile Val Val Ser Met
    130                 135                 140

Asn Tyr Arg Val Gly Ala Leu Gly Phe Leu Ala Leu Pro Gly Asn Pro
145                 150                 155                 160

Glu Ala Pro Gly Asn Met Gly Leu Phe Asp Gln Gln Leu Ala Leu Gln
                165                 170                 175

Trp Val Gln Lys Asn Ile Ala Ala Phe Gly Gly Asn Pro Lys Ser Val
            180                 185                 190

Thr Leu Phe Gly Glu Ser Ser Gly Ala Ala Ser Val Ser Leu His Leu
        195                 200                 205

Leu Ser Pro Gly Ser His Ser Leu Phe Thr Arg Ala Ile Leu Gln Ser
    210                 215                 220

Gly Ser Pro Asn Ala Pro Trp Ala Val Thr Ser Leu Tyr Glu Ala Arg
225                 230                 235                 240

Asn Arg Thr Leu Asn Leu Ala Lys Leu Thr Gly Cys Ser Arg Glu Asn
                245                 250                 255

Glu Thr Glu Ile Ile Lys Cys Leu Arg Asn Lys Asp Pro Gln Glu Ile
            260                 265                 270

Leu Leu Asn Glu Ala Phe Val Val Pro Tyr Gly Thr Pro Leu Gly Val
        275                 280                 285

Asn Phe Gly Pro Thr Val Asp Gly Asp Phe Leu Thr Asp Met Pro Asp
    290                 295                 300

Ile Leu Leu Glu Leu Gly Gln Phe Lys Lys Thr Gln Ile Leu Val Gly
305                 310                 315                 320

Val Asn Lys Asp Glu Gly Thr Trp Phe Leu Val Gly Gly Ala Pro Gly
                325                 330                 335

Phe Ser Lys Asp Asn Asn Ser Ile Ile Thr Arg Lys Glu Phe Gln Glu
            340                 345                 350

Gly Leu Lys Ile Phe Phe Pro Gly Val Ser Glu Phe Gly Lys Glu Ser
        355                 360                 365

Ile Leu Phe His Tyr Thr Asp Trp Val Asp Asp Gln Arg Pro Glu Asn
    370                 375                 380
```

```
Tyr Arg Glu Ala Leu Gly Asp Val Val Gly Asp Tyr Asn Phe Ile Cys
385                 390                 395                 400

Pro Ala Leu Glu Phe Thr Lys Lys Phe Ser Glu Trp Gly Asn Asn Ala
                405                 410                 415

Phe Phe Tyr Tyr Phe Glu His Arg Ser Ser Lys Leu Pro Trp Pro Glu
            420                 425                 430

Trp Met Gly Val Met His Gly Tyr Glu Ile Glu Phe Val Phe Gly Leu
        435                 440                 445

Pro Leu Glu Arg Arg Asp Asn Tyr Thr Lys Ala Glu Glu Ile Leu Ser
    450                 455                 460

Arg Ser Ile Val Lys Arg Trp Ala Asn Phe Ala Lys Tyr Gly Asn Pro
465                 470                 475                 480

Asn Glu Thr Gln Asn Asn Ser Thr Ser Trp Pro Val Phe Lys Ser Thr
                485                 490                 495

Glu Gln Lys Tyr Leu Thr Leu Asn Thr Glu Ser Thr Arg Ile Met Thr
            500                 505                 510

Lys Leu Arg Ala Gln Gln Cys Arg Phe Trp Thr Ser Phe Phe Pro Lys
        515                 520                 525

Val Leu Glu Met Thr Gly Asn Ile Asp Glu Ala Glu Trp Glu Trp Lys
    530                 535                 540

Ala Gly Phe His Arg Trp Asn Asn Tyr Met Met Asp Trp Lys Asn Gln
545                 550                 555                 560

Phe Asn Asp Tyr Thr Ser Lys Lys Glu Ser Cys Val Gly Leu
                565                 570

<210> SEQ ID NO 9
<211> LENGTH: 1722
<212> TYPE: DNA
<213> ORGANISM: Artificial Sequence
<220> FEATURE:
<223> OTHER INFORMATION: mutant of human BChE

<400> SEQUENCE: 9
gaagatgaca tcataattgc aacaaagaat ggaaaagtca gagggatgaa cttgacagtt      60
tttggtggca cggtaacagc cttttcttgga attccctatg cacagccacc tcttggtaga    120
cttcgattca aaaagccaca gtctctgacc aagtggtctg atatttggaa tgccacaaaa    180
tatgcaaatt cttgctgtca gaacatagat caaagttttc caggcttcca tggatcagag    240
atgtggaacc caaacactga cctcagtgaa gactgtttat atctaaatgt atggattcca    300
gcacctaaac caaaaaatgc cactgtattg atatggattt atggtggtgg tttttcaaact   360
ggaacatcat ctttacatgt ttatgatggc aagtttctgg ctcgggttga aagagttatt    420
gtagtgtcaa tgaactatag ggtgggtgcc ctaggattct tagctttgcc aggaaatcct    480
gaggctccag ggaacatggg tttatttgat aacagttgg ctcttcagtg ggttcaaaaa      540
aatatagcag cctttggtgg aaatcctaaa agtgtaactc tctttggaga agttccggga    600
gcagcttcag ttagcctgca tttgctttct cctggaagcc attcattgtt caccagagcc    660
attctgcaaa gtggttccgc taatgctcct tgggcggtaa catctcttta tgaagctagg    720
aacagaacgt tgaacttagc taaattgact ggttgctcta gagagaatga gactgaaata    780
atcaagtgtc ttagaaataa agatcccaa gaaattcttc tgaatgaagc atttgttgtc      840
ccctatggga ctggtttggg tgtaaacttt ggtccgaccg tggatggtga ttttctcact    900
gacatgccag acatattact tgaacttgga caatttaaaa aaacccagat tttggtgggt    960
```

-continued

```
gttaataaag atgaagggac atggttttta gtcggtggtg ctcctggctt cagcaaagat    1020
aacaatagta tcataactag aaaagaattt caggaaggtt taaaaatatt ttttccagga    1080
gtgagtgagt ttggaaagga atccatcctt tttcattaca cagactgggt agatgatcag    1140
agacctgaaa actaccgtga ggccttgggt gatgttgttg gggattataa tttcatatgc    1200
cctgccttgg agttcaccaa gaagttctca gaatggggaa ataatgcctt tttctactat    1260
tttgaacacc gatcctccaa acttccgtgg ccagaatgga tgggagtgat gcatggctat    1320
gaaattgaat ttgtctttgg tttacctctg gaaagaagag ataattacac aaaagccgag    1380 gaaatttga gtagatccat agtgaaacgg tgggcaaatt ttgcaaaata tgggaatcca    1440
aatgagactc agaacaatag cacaagctgg cctgtcttca aaagcactga acaaaaatat    1500
ctaaccttga atacagagtc aacaagaata atgacgaaac tacgtgctca acaatgtcga    1560
ttctggacat catttttccc aaaagtcttg gaaatgacag gaaatattga tgaagcagaa    1620
tgggagtgga aagcaggatt ccatcgctgg aacaattaca tgatggactg gaaaaatcaa    1680
tttaacgatt acactagcaa gaaagaaagt tgtgtgggtc tc                      1722
```

<210> SEQ ID NO 10
<211> LENGTH: 574
<212> TYPE: PRT
<213> ORGANISM: Artificial Sequence
<220> FEATURE:
<223> OTHER INFORMATION: mutant of human BChE

<400> SEQUENCE: 10

```
Glu Asp Asp Ile Ile Ile Ala Thr Lys Asn Gly Lys Val Arg Gly Met
1               5                   10                  15

Asn Leu Thr Val Phe Gly Gly Thr Val Thr Ala Phe Leu Gly Ile Pro
            20                  25                  30

Tyr Ala Gln Pro Pro Leu Gly Arg Leu Arg Phe Lys Lys Pro Gln Ser
        35                  40                  45

Leu Thr Lys Trp Ser Asp Ile Trp Asn Ala Thr Lys Tyr Ala Asn Ser
    50                  55                  60

Cys Cys Gln Asn Ile Asp Gln Ser Phe Pro Gly Phe His Gly Ser Glu
65                  70                  75                  80

Met Trp Asn Pro Asn Thr Asp Leu Ser Glu Asp Cys Leu Tyr Leu Asn
                85                  90                  95

Val Trp Ile Pro Ala Pro Lys Pro Lys Asn Ala Thr Val Leu Ile Trp
            100                 105                 110

Ile Tyr Gly Gly Gly Phe Gln Thr Gly Thr Ser Ser Leu His Val Tyr
        115                 120                 125

Asp Gly Lys Phe Leu Ala Arg Val Glu Arg Val Ile Val Val Ser Met
    130                 135                 140

Asn Tyr Arg Val Gly Ala Leu Gly Phe Leu Ala Leu Pro Gly Asn Pro
145                 150                 155                 160

Glu Ala Pro Gly Asn Met Gly Leu Phe Asp Gln Gln Leu Ala Leu Gln
                165                 170                 175

Trp Val Gln Lys Asn Ile Ala Ala Phe Gly Gly Asn Pro Lys Ser Val
            180                 185                 190

Thr Leu Phe Gly Glu Ser Ser Gly Ala Ala Ser Val Ser Leu His Leu
        195                 200                 205

Leu Ser Pro Gly Ser His Ser Leu Phe Thr Arg Ala Ile Leu Gln Ser
    210                 215                 220

Gly Ser Ala Asn Ala Pro Trp Ala Val Thr Ser Leu Tyr Glu Ala Arg
```

-continued

```
                225                 230                 235                 240

Asn Arg Thr Leu Asn Leu Ala Lys Leu Thr Gly Cys Ser Arg Glu Asn
                245                 250                 255

Glu Thr Glu Ile Ile Lys Cys Leu Arg Asn Lys Asp Pro Gln Glu Ile
            260                 265                 270

Leu Leu Asn Glu Ala Phe Val Val Pro Tyr Gly Thr Gly Leu Gly Val
        275                 280                 285

Asn Phe Gly Pro Thr Val Asp Gly Asp Phe Leu Thr Asp Met Pro Asp
    290                 295                 300

Ile Leu Leu Glu Leu Gly Gln Phe Lys Lys Thr Gln Ile Leu Val Gly
305                 310                 315                 320

Val Asn Lys Asp Glu Gly Thr Trp Phe Leu Val Gly Gly Ala Pro Gly
                325                 330                 335

Phe Ser Lys Asp Asn Asn Ser Ile Ile Thr Arg Lys Glu Phe Gln Glu
                340                 345                 350

Gly Leu Lys Ile Phe Phe Pro Gly Val Ser Glu Phe Gly Lys Glu Ser
            355                 360                 365

Ile Leu Phe His Tyr Thr Asp Trp Val Asp Asp Gln Arg Pro Glu Asn
        370                 375                 380

Tyr Arg Glu Ala Leu Gly Asp Val Val Gly Asp Tyr Asn Phe Ile Cys
385                 390                 395                 400

Pro Ala Leu Glu Phe Thr Lys Lys Phe Ser Glu Trp Gly Asn Asn Ala
                405                 410                 415

Phe Phe Tyr Tyr Phe Glu His Arg Ser Ser Lys Leu Pro Trp Pro Glu
                420                 425                 430

Trp Met Gly Val Met His Gly Tyr Glu Ile Glu Phe Val Phe Gly Leu
            435                 440                 445

Pro Leu Glu Arg Arg Asp Asn Tyr Thr Lys Ala Glu Glu Ile Leu Ser
        450                 455                 460

Arg Ser Ile Val Lys Arg Trp Ala Asn Phe Ala Lys Tyr Gly Asn Pro
465                 470                 475                 480

Asn Glu Thr Gln Asn Asn Ser Thr Ser Trp Pro Val Phe Lys Ser Thr
                485                 490                 495

Glu Gln Lys Tyr Leu Thr Leu Asn Thr Glu Ser Thr Arg Ile Met Thr
            500                 505                 510

Lys Leu Arg Ala Gln Gln Cys Arg Phe Trp Thr Ser Phe Phe Pro Lys
        515                 520                 525

Val Leu Glu Met Thr Gly Asn Ile Asp Glu Ala Glu Trp Glu Trp Lys
    530                 535                 540

Ala Gly Phe His Arg Trp Asn Asn Tyr Met Met Asp Trp Lys Asn Gln
545                 550                 555                 560

Phe Asn Asp Tyr Thr Ser Lys Lys Glu Ser Cys Val Gly Leu
                565                 570
```

<210> SEQ ID NO 11
<211> LENGTH: 1722
<212> TYPE: DNA
<213> ORGANISM: Artificial Sequence
<220> FEATURE:
<223> OTHER INFORMATION: mutant of human BChE

<400> SEQUENCE: 11
gaagatgaca tcataattgc aacaaagaat ggaaaagtca gagggatgaa cttgacagtt      60
tttggtggca cggtaacagc ctttcttgga attccctatg cacagccacc tcttggtaga     120

```
cttcgattca aaaagccaca gtctctgacc aagtggtctg atatttggaa tgccacaaaa    180
tatgcaaatt cttgctgtca gaacatagat caaagttttc caggcttcca tggatcagag    240
atgtggaacc caaacactga cctcagtgaa gactgtttat atctaaatgt atggattcca    300
gcacctaaac caaaaaatgc cactgtattg atatggattt atggtggtgg ttttcaaact    360
ggaacatcat ctttacatgt ttatgatggc aagtttctgg ctcgggttga agagttatt    420 gtagtgtcaa tgaactatag ggtgggtgcc ctaggattct tagctttgcc aggaaatcct    480
gaggctccag ggaacatggg tttatttgat caacagttgg ctcttcagtg ggttcaaaaa    540
aatatagcag cctttggtgg aaatcctaaa agtgtaactc tctttggaga aagttccgga    600
gcagcttcag ttagcctgca tttgctttct cctggaagcc attcattgtt caccagagcc    660
attctgcaaa gtggttccgc taatgctcct tgggcggtaa catctcttta tgaagctagg    720
aacagaacgt tgaacttagc taaattgact ggttgctcta gagagaatga gactgaaata    780
atcaagtgtc ttagaaataa agatcccaa gaaattcttc tgaatgaagc atttgttgtc    840
ccctatggga ctcctatggg tgtaaacttt ggtccgaccg tggatggtga ttttctcact    900
gacatgccag acatattact tgaacttgga caatttaaaa aaacccagat ttggtgggt    960 gttaataaag atgaagggac atggttttta gtcggtggtg ctcctggctt cagcaaagat   1020
aacaatagta tcataactag aaaagaattt caggaaggtt taaaaatatt ttttccagga   1080
gtgagtgagt ttggaaagga atccatcctt tttcattaca cagactgggt agatgatcag   1140
agacctgaaa actaccgtga ggccttgggt gatgttgttg gggattataa tttcatatgc   1200
cctgccttgg agttcaccaa gaagttctca gaatgggaa ataatgcctt tttctactat   1260
tttgaacacc gatcctccaa acttccgtgg ccagaatgga tgggagtgat gcatggctat   1320
gaaattgaat ttgtctttgg tttacctctg gaaagaagag ataattacac aaaagccgag   1380
gaaattttga gtagatccat agtgaaacgg tgggcaaatt ttgcaaaata tgggaatcca   1440
aatgagactc agaacaatag cacaagctgg cctgtcttca aaagcactga caaaaatat   1500 ctaaccttga atacagagtc aacaagaata atgacgaaac tacgtgctca acaatgtcga   1560
ttctggacat cattttttcc aaaagtcttg gaaatgacag gaaatattga tgaagcagaa   1620
tgggagtgga aagcaggatt ccatcgctgg aacaattaca tgatggactg gaaaaatcaa   1680
tttaacgatt acactagcaa gaaagaaagt tgtgtgggtc tc                      1722
```

<210> SEQ ID NO 12
<211> LENGTH: 574
<212> TYPE: PRT
<213> ORGANISM: Artificial Sequence
<220> FEATURE:
<223> OTHER INFORMATION: mutant of human BChE

<400> SEQUENCE: 12

```
Glu Asp Asp Ile Ile Ile Ala Thr Lys Asn Gly Lys Val Arg Gly Met
1               5                   10                  15

Asn Leu Thr Val Phe Gly Gly Thr Val Thr Ala Phe Leu Gly Ile Pro
            20                  25                  30

Tyr Ala Gln Pro Pro Leu Gly Arg Leu Arg Phe Lys Lys Pro Gln Ser
        35                  40                  45

Leu Thr Lys Trp Ser Asp Ile Trp Asn Ala Thr Lys Tyr Ala Asn Ser
    50                  55                  60

Cys Cys Gln Asn Ile Asp Gln Ser Phe Pro Gly Phe His Gly Ser Glu
65                  70                  75                  80
```

-continued

```
Met Trp Asn Pro Asn Thr Asp Leu Ser Glu Asp Cys Leu Tyr Leu Asn
                85                  90                  95
Val Trp Ile Pro Ala Pro Lys Pro Lys Asn Ala Thr Val Leu Ile Trp
            100                 105                 110
Ile Tyr Gly Gly Gly Phe Gln Thr Gly Thr Ser Ser Leu His Val Tyr
        115                 120                 125
Asp Gly Lys Phe Leu Ala Arg Val Glu Arg Val Ile Val Val Ser Met
    130                 135                 140
Asn Tyr Arg Val Gly Ala Leu Gly Phe Leu Ala Leu Pro Gly Asn Pro
145                 150                 155                 160
Glu Ala Pro Gly Asn Met Gly Leu Phe Asp Gln Gln Leu Ala Leu Gln
                165                 170                 175
Trp Val Gln Lys Asn Ile Ala Ala Phe Gly Gly Asn Pro Lys Ser Val
            180                 185                 190
Thr Leu Phe Gly Glu Ser Ser Gly Ala Ala Ser Val Ser Leu His Leu
        195                 200                 205
Leu Ser Pro Gly Ser His Ser Leu Phe Thr Arg Ala Ile Leu Gln Ser
    210                 215                 220
Gly Ser Ala Asn Ala Pro Trp Ala Val Thr Ser Leu Tyr Glu Ala Arg
225                 230                 235                 240
Asn Arg Thr Leu Asn Leu Ala Lys Leu Thr Gly Cys Ser Arg Glu Asn
                245                 250                 255
Glu Thr Glu Ile Ile Lys Cys Leu Arg Asn Lys Asp Pro Gln Glu Ile
            260                 265                 270
Leu Leu Asn Glu Ala Phe Val Val Pro Tyr Gly Thr Pro Met Gly Val
        275                 280                 285
Asn Phe Gly Pro Thr Val Asp Gly Asp Phe Leu Thr Asp Met Pro Asp
    290                 295                 300
Ile Leu Leu Glu Leu Gly Gln Phe Lys Lys Thr Gln Ile Leu Val Gly
305                 310                 315                 320
Val Asn Lys Asp Glu Gly Thr Trp Phe Leu Val Gly Gly Ala Pro Gly
                325                 330                 335
Phe Ser Lys Asp Asn Asn Ser Ile Ile Thr Arg Lys Glu Phe Gln Glu
            340                 345                 350
Gly Leu Lys Ile Phe Phe Pro Gly Val Ser Glu Phe Gly Lys Glu Ser
        355                 360                 365
Ile Leu Phe His Tyr Thr Asp Trp Val Asp Asp Gln Arg Pro Glu Asn
    370                 375                 380
Tyr Arg Glu Ala Leu Gly Asp Val Val Gly Asp Tyr Asn Phe Ile Cys
385                 390                 395                 400
Pro Ala Leu Glu Phe Thr Lys Lys Phe Ser Glu Trp Gly Asn Asn Ala
                405                 410                 415
Phe Phe Tyr Tyr Phe Glu His Arg Ser Ser Lys Leu Pro Trp Pro Glu
            420                 425                 430
Trp Met Gly Val Met His Gly Tyr Glu Ile Glu Phe Val Phe Gly Leu
        435                 440                 445
Pro Leu Glu Arg Arg Asp Asn Tyr Thr Lys Ala Glu Ile Leu Ser
    450                 455                 460
Arg Ser Ile Val Lys Arg Trp Ala Asn Phe Ala Lys Tyr Gly Asn Pro
465                 470                 475                 480
Asn Glu Thr Gln Asn Asn Ser Thr Ser Trp Pro Val Phe Lys Ser Thr
                485                 490                 495
Glu Gln Lys Tyr Leu Thr Leu Asn Thr Glu Ser Thr Arg Ile Met Thr
```

```
              500             505             510
Lys Leu Arg Ala Gln Gln Cys Arg Phe Trp Thr Ser Phe Phe Pro Lys
            515                 520                 525

Val Leu Glu Met Thr Gly Asn Ile Asp Glu Ala Glu Trp Glu Trp Lys
            530                 535                 540

Ala Gly Phe His Arg Trp Asn Asn Tyr Met Met Asp Trp Lys Asn Gln
545                 550                 555                 560

Phe Asn Asp Tyr Thr Ser Lys Lys Glu Ser Cys Val Gly Leu
                565                 570
```

<210> SEQ ID NO 13
<211> LENGTH: 1722
<212> TYPE: DNA
<213> ORGANISM: Artificial Sequence
<220> FEATURE:
<223> OTHER INFORMATION: mutant of human BChE

<400> SEQUENCE: 13

```
gaagatgaca tcataattgc aacaaagaat ggaaaagtca gagggatgaa cttgacagtt      60
tttggtggca cggtaacagc ctttcttgga attccctatg cacagccacc tcttggtaga     120
cttcgattca aaaagccaca gtctctgacc aagtggtctg atatttggaa tgccacaaaa     180
tatgcaaatt cttgctgtca gaacatagat caaagttttc caggcttcca tggatcagag     240
atgtggaacc caaacactga cctcagtgaa gactgtttat atctaaatgt atggattcca     300
gcacctaaac aaaaaatgc cactgtattg atatggattt atggtggtgg ttttcaaact     360
ggaacatcat ctttacatgt ttatgatggc aagtttctgg ctcgggttga agagttatt     420
gtagtgtcaa tgaactatag ggtgggtgcc ctaggattct tagctttgcc aggaaatcct     480
gaggctccag ggaacatggg tttatttgat caacagttgg ctcttcagtg ggttcaaaaa     540
aatatagcag cctttggtgg aaatcctaaa agtgtaactc tctttggaga agttccgga     600
gcagcttcag ttagcctgca tttgctttct cctggaagcc attcattgtt caccagagcc     660
attctgcaaa gtggttcctt taatgctcct tgggcggtaa catctcttta tgaagctagg     720
aacagaacgt tgaacttagc taaattgact ggttgctcta gagagaatga gactgaaata     780
atcaagtgtc ttagaaataa agatccccaa gaaattcttc tgaatgaagc atttgttgtc     840
ccctatggga ctcagttggg tgtaaacttt ggtccgaccg tggatggtga ttttctcact     900
gacatgccag acatattact tgaacttgga caatttaaaa aaacccagat ttggtgggt     960
gttaataaag atgaagggac atggttttta gtcggtggtg ctcctggctt cagcaaagat    1020
aacaatagta tcataactag aaaagaattt caggaaggtt taaaatatt tttttccagga    1080
gtgagtgagt ttgaaaagga atccatcctt tttcattaca cagactggt agatgatcag    1140
agacctgaaa actaccgtga ggccttgggt gatgttgttg gggattataa tttcatatgc    1200
cctgccttgg agttcaccaa gaagttctca gaatggggaa ataatgcctt ttctactat    1260
tttgaacacc gatcctccaa acttccgtgg ccagaatgga tgggagtgat gcatggctat    1320
gaaattgaat ttgtctttgg tttacctctg gaaagaagag ataattacac aaaagccgag    1380
gaaattttga gtagatccat agtgaaacgg tgggcaaatt ttgcaaaata tgggaatcca    1440
aatgagactc agaacaatag cacaagctgg cctgtcttca aaagcactga caaaaatat    1500
ctaaccttga atacagagtc aacaagaata atgacgaaac tacgtgctca acaatgtcga    1560
ttctggacat cattttttcc aaaagtcttg gaaatgacag gaaatattga tgaagcagaa    1620
tgggagtgga agcaggatt ccatcgctgg aacaattaca tgatggactg gaaaaatcaa    1680
```
tttaacgatt acactagcaa gaaagaaagt tgtgtgggtc tc        1722

<210> SEQ ID NO 14
<211> LENGTH: 574
<212> TYPE: PRT
<213> ORGANISM: Artificial Sequence
<220> FEATURE:
<223> OTHER INFORMATION: mutant of human BChE

<400> SEQUENCE: 14

Glu Asp Asp Ile Ile Ile Ala Thr Lys Asn Gly Lys Val Arg Gly Met
1               5                   10                  15

Asn Leu Thr Val Phe Gly Gly Thr Val Thr Ala Phe Leu Gly Ile Pro
            20                  25                  30

Tyr Ala Gln Pro Pro Leu Gly Arg Leu Arg Phe Lys Lys Pro Gln Ser
        35                  40                  45

Leu Thr Lys Trp Ser Asp Ile Trp Asn Ala Thr Lys Tyr Ala Asn Ser
    50                  55                  60

Cys Cys Gln Asn Ile Asp Gln Ser Phe Pro Gly Phe His Gly Ser Glu
65                  70                  75                  80

Met Trp Asn Pro Asn Thr Asp Leu Ser Glu Asp Cys Leu Tyr Leu Asn
                85                  90                  95

Val Trp Ile Pro Ala Pro Lys Pro Lys Asn Ala Thr Val Leu Ile Trp
            100                 105                 110

Ile Tyr Gly Gly Gly Phe Gln Thr Gly Thr Ser Ser Leu His Val Tyr
        115                 120                 125

Asp Gly Lys Phe Leu Ala Arg Val Glu Arg Val Ile Val Val Ser Met
    130                 135                 140

Asn Tyr Arg Val Gly Ala Leu Gly Phe Leu Ala Leu Pro Gly Asn Pro
145                 150                 155                 160

Glu Ala Pro Gly Asn Met Gly Leu Phe Asp Gln Gln Leu Ala Leu Gln
                165                 170                 175

Trp Val Gln Lys Asn Ile Ala Ala Phe Gly Gly Asn Pro Lys Ser Val
            180                 185                 190

Thr Leu Phe Gly Glu Ser Ser Gly Ala Ala Ser Val Ser Leu His Leu
        195                 200                 205

Leu Ser Pro Gly Ser His Ser Leu Phe Thr Arg Ala Ile Leu Gln Ser
    210                 215                 220

Gly Ser Phe Asn Ala Pro Trp Ala Val Thr Ser Leu Tyr Glu Ala Arg
225                 230                 235                 240

Asn Arg Thr Leu Asn Leu Ala Lys Leu Thr Gly Cys Ser Arg Glu Asn
                245                 250                 255

Glu Thr Glu Ile Ile Lys Cys Leu Arg Asn Lys Asp Pro Gln Glu Ile
            260                 265                 270

Leu Leu Asn Glu Ala Phe Val Val Pro Tyr Gly Thr Gln Leu Gly Val
        275                 280                 285

Asn Phe Gly Pro Thr Val Asp Gly Asp Phe Leu Thr Asp Met Pro Asp
    290                 295                 300

Ile Leu Leu Glu Leu Gly Gln Phe Lys Lys Thr Gln Ile Leu Val Gly
305                 310                 315                 320

Val Asn Lys Asp Glu Gly Thr Trp Phe Leu Val Gly Gly Ala Pro Gly
                325                 330                 335

Phe Ser Lys Asp Asn Asn Ser Ile Ile Thr Arg Lys Glu Phe Gln Glu
            340                 345                 350

```
Gly Leu Lys Ile Phe Phe Pro Gly Val Ser Glu Phe Gly Lys Glu Ser
            355                 360                 365
Ile Leu Phe His Tyr Thr Asp Trp Val Asp Asp Gln Arg Pro Glu Asn
            370                 375                 380
Tyr Arg Glu Ala Leu Gly Asp Val Val Gly Asp Tyr Asn Phe Ile Cys
385                 390                 395                 400
Pro Ala Leu Glu Phe Thr Lys Lys Phe Ser Glu Trp Gly Asn Asn Ala
                405                 410                 415
Phe Phe Tyr Tyr Phe Glu His Arg Ser Ser Lys Leu Pro Trp Pro Glu
            420                 425                 430
Trp Met Gly Val Met His Gly Tyr Glu Ile Glu Phe Val Phe Gly Leu
            435                 440                 445
Pro Leu Glu Arg Arg Asp Asn Tyr Thr Lys Ala Glu Glu Ile Leu Ser
            450                 455                 460
Arg Ser Ile Val Lys Arg Trp Ala Asn Phe Ala Lys Tyr Gly Asn Pro
465                 470                 475                 480
Asn Glu Thr Gln Asn Asn Ser Thr Ser Trp Pro Val Phe Lys Ser Thr
                485                 490                 495
Glu Gln Lys Tyr Leu Thr Leu Asn Thr Glu Ser Thr Arg Ile Met Thr
            500                 505                 510
Lys Leu Arg Ala Gln Gln Cys Arg Phe Trp Thr Ser Phe Phe Pro Lys
            515                 520                 525
Val Leu Glu Met Thr Gly Asn Ile Asp Glu Ala Glu Trp Glu Trp Lys
            530                 535                 540
Ala Gly Phe His Arg Trp Asn Asn Tyr Met Met Asp Trp Lys Asn Gln
545                 550                 555                 560
Phe Asn Asp Tyr Thr Ser Lys Lys Glu Ser Cys Val Gly Leu
                565                 570

<210> SEQ ID NO 15
<211> LENGTH: 1722
<212> TYPE: DNA
<213> ORGANISM: Artificial Sequence
<220> FEATURE:
<223> OTHER INFORMATION: mutant of human BChE

<400> SEQUENCE: 15
gaagatgaca tcataattgc aacaaagaat ggaaaagtca gagggatgaa cttgacagtt      60
tttggtggca cggtaacagc ctttcttgga attccctatg cacagccacc tcttggtaga     120
cttcgattca aaaagccaca gtctctgacc aagtggtctg atatttggaa tgccacaaaa     180
tatgcaaatt cttgctgtca gaacatagat caaagttttc caggcttcca tggatcagag     240
atgtggaacc caaacactga cctcagtgaa gactgtttat atctaaatgt atggattcca     300
gcacctaaac caaaaaatgc cactgtattg atatggattt atggtggtgg ttttcaaact     360
ggaacatcat ctttacatgt ttatgatggc aagtttctgg ctcgggttga agagttatt      420 gtagtgtcaa tgaactatag ggtgggtgcc ctaggattct tagctttgcc aggaaatcct     480
gaggctccag ggaacatggg tttatttgat aacagttggc tcttcagtgg gttcaaaaa      540 aatatagcag cctttggtgg aaatcctaaa agtgtaactc tctttggaga agttccgga      600 gcagcttcag ttagcctgca tttgctttct cctggaagcc attcattgtt caccagagcc     660
attctgcaaa gtggttcctt taatgctcct tgggcggtaa catctcttta tgaagctagg     720
aacagaacgt tgaacttagc taaattgact ggttgctcta gagagaatga gactgaaata     780
atcaagtgtc ttagaaataa agatcccaa gaaattcttc tgaatgaagc atttgttgtc     840
```

```
ccctatggga ctatcttggg tgtaaacttt ggtccgaccg tggatggtga ttttctcact    900
gacatgccag acatattact tgaacttgga caatttaaaa aaacccagat tttggtgggt    960
gttaataaag atgaagggac atggttttta gtcggtggtg ctcctggctt cagcaaagat   1020
aacaatagta tcataactag aaaagaattt caggaaggtt taaaaatatt ttttccagga   1080
gtgagtgagt ttggaaagga atccatcctt tttcattaca cagactgggt agatgatcag   1140
agacctgaaa actaccgtga ggccttgggt gatgttgttg gggattataa tttcatatgc   1200
cctgccttgg agttcaccaa gaagttctca gaatggggaa ataatgcctt tttctactat   1260
tttgaacacc gatcctccaa acttccgtgg ccagaatgga tgggagtgat gcatggctat   1320
gaaattgaat tgtctttgg tttacctctg gaaagaagag ataattacac aaaagccgag   1380
gaaatttga gtagatccat agtgaaacgg tgggcaaatt ttgcaaaata tgggaatcca   1440
aatgagactc agaacaatag cacaagctgg cctgtcttca aaagcactga acaaaaatat   1500
ctaaccttga atacagagtc aacaagaata atgacgaaac tacgtgctca acaatgtcga   1560
ttctggacat catttttttcc aaaagtcttg gaaatgacag gaaatattga tgaagcagaa   1620
tgggagtgga aagcaggatt ccatcgctgg aacaattaca tgatggactg gaaaaatcaa   1680
tttaacgatt acactagcaa gaaagaaagt tgtgtgggtc tc                      1722
```

<210> SEQ ID NO 16
<211> LENGTH: 574
<212> TYPE: PRT
<213> ORGANISM: Artificial Sequence
<220> FEATURE:
<223> OTHER INFORMATION: mutant of human BChE

<400> SEQUENCE: 16

```
Glu Asp Asp Ile Ile Ile Ala Thr Lys Asn Gly Lys Val Arg Gly Met
1               5                   10                  15

Asn Leu Thr Val Phe Gly Gly Thr Val Thr Ala Phe Leu Gly Ile Pro
            20                  25                  30

Tyr Ala Gln Pro Pro Leu Gly Arg Leu Arg Phe Lys Lys Pro Gln Ser
        35                  40                  45

Leu Thr Lys Trp Ser Asp Ile Trp Asn Ala Thr Lys Tyr Ala Asn Ser
    50                  55                  60

Cys Cys Gln Asn Ile Asp Gln Ser Phe Pro Gly Phe His Gly Ser Glu
65                  70                  75                  80

Met Trp Asn Pro Asn Thr Asp Leu Ser Glu Asp Cys Leu Tyr Leu Asn
                85                  90                  95

Val Trp Ile Pro Ala Pro Lys Pro Lys Asn Ala Thr Val Leu Ile Trp
            100                 105                 110

Ile Tyr Gly Gly Gly Phe Gln Thr Gly Thr Ser Ser Leu His Val Tyr
        115                 120                 125

Asp Gly Lys Phe Leu Ala Arg Val Glu Arg Val Ile Val Val Ser Met
    130                 135                 140

Asn Tyr Arg Val Gly Ala Leu Gly Phe Leu Ala Leu Pro Gly Asn Pro
145                 150                 155                 160

Glu Ala Pro Gly Asn Met Gly Leu Phe Asp Gln Gln Leu Ala Leu Gln
                165                 170                 175

Trp Val Gln Lys Asn Ile Ala Ala Phe Gly Gly Asn Pro Lys Ser Val
            180                 185                 190

Thr Leu Phe Gly Glu Ser Ser Gly Ala Ala Ser Val Ser Leu His Leu
        195                 200                 205
```

```
Leu Ser Pro Gly Ser His Ser Leu Phe Thr Arg Ala Ile Leu Gln Ser
    210                 215                 220
Gly Ser Phe Asn Ala Pro Trp Ala Val Thr Ser Leu Tyr Glu Ala Arg
225                 230                 235                 240
Asn Arg Thr Leu Asn Leu Ala Lys Leu Thr Gly Cys Ser Arg Glu Asn
                245                 250                 255
Glu Thr Glu Ile Ile Lys Cys Leu Arg Asn Lys Asp Pro Gln Glu Ile
                260                 265                 270
Leu Leu Asn Glu Ala Phe Val Val Pro Tyr Gly Thr Ile Leu Gly Val
            275                 280                 285
Asn Phe Gly Pro Thr Val Asp Gly Asp Phe Leu Thr Asp Met Pro Asp
290                 295                 300
Ile Leu Leu Glu Leu Gly Gln Phe Lys Lys Thr Gln Ile Leu Val Gly
305                 310                 315                 320
Val Asn Lys Asp Glu Gly Thr Trp Phe Leu Val Gly Gly Ala Pro Gly
                325                 330                 335
Phe Ser Lys Asp Asn Asn Ser Ile Ile Thr Arg Lys Glu Phe Gln Glu
                340                 345                 350
Gly Leu Lys Ile Phe Phe Pro Gly Val Ser Glu Phe Gly Lys Glu Ser
            355                 360                 365
Ile Leu Phe His Tyr Thr Asp Trp Val Asp Asp Gln Arg Pro Glu Asn
        370                 375                 380
Tyr Arg Glu Ala Leu Gly Asp Val Val Gly Asp Tyr Asn Phe Ile Cys
385                 390                 395                 400
Pro Ala Leu Glu Phe Thr Lys Lys Phe Ser Glu Trp Gly Asn Asn Ala
                405                 410                 415
Phe Phe Tyr Tyr Phe Glu His Arg Ser Ser Lys Leu Pro Trp Pro Glu
                420                 425                 430
Trp Met Gly Val Met His Gly Tyr Glu Ile Glu Phe Val Phe Gly Leu
            435                 440                 445
Pro Leu Glu Arg Arg Asp Asn Tyr Thr Lys Ala Glu Glu Ile Leu Ser
        450                 455                 460
Arg Ser Ile Val Lys Arg Trp Ala Asn Phe Ala Lys Tyr Gly Asn Pro
465                 470                 475                 480
Asn Glu Thr Gln Asn Asn Ser Thr Ser Trp Pro Val Phe Lys Ser Thr
                485                 490                 495
Glu Gln Lys Tyr Leu Thr Leu Asn Thr Glu Ser Thr Arg Ile Met Thr
                500                 505                 510
Lys Leu Arg Ala Gln Gln Cys Arg Phe Trp Thr Ser Phe Phe Pro Lys
            515                 520                 525
Val Leu Glu Met Thr Gly Asn Ile Asp Glu Ala Glu Trp Glu Trp Lys
        530                 535                 540
Ala Gly Phe His Arg Trp Asn Asn Tyr Met Met Asp Trp Lys Asn Gln
545                 550                 555                 560
Phe Asn Asp Tyr Thr Ser Lys Lys Glu Ser Cys Val Gly Leu
                565                 570

<210> SEQ ID NO 17
<211> LENGTH: 1722
<212> TYPE: DNA
<213> ORGANISM: Artificial Sequence
<220> FEATURE:
<223> OTHER INFORMATION: mutant of human BChE

<400> SEQUENCE: 17
```

```
gaagatgaca tcataattgc aacaaagaat ggaaaagtca gagggatgaa cttgacagtt      60
tttggtggca cggtaacagc ctttcttgga attccctatg cacagccacc tcttggtaga     120
cttcgattca aaaagccaca gtctctgacc aagtggtctg atatttggaa tgccacaaaa     180
tatgcaaatt cttgctgtca gaacatagat caaagttttc caggcttcca tggatcagag     240
atgtggaacc caaacactga cctcagtgaa gactgtttat atctaaatgt atggattcca     300
gcacctaaac caaaaaatgc cactgtattg atatggattt atggtggtgg ttttcaaact     360
ggaacatcat ctttacatgt ttatgatggc aagtttctgg ctcgggttga aagagttatt     420
gtagtgtcaa tgaactatag ggtgggtgcc ctaggattct tagctttgcc aggaaatcct     480
gaggctccag ggaacatggg tttatttgat aacagttgg ctcttcagtg ggttcaaaaa     540
aatatagcag cctttggtgg aaatcctaaa agtgtaactc tctttggaga aagttccgga     600
gcagcttcag ttagcctgca tttgctttct cctggaagcc attcattgtt caccagagcc     660
attctgcaaa gtggttccgg taatgctcct tgggcggtaa catctcttta tgaagctagg     720
aacagaacgt tgaacttagc taaattgact ggttgctcta gagagaatga gactgaaata     780
atcaagtgtc ttagaaataa agatccccaa gaaattcttc tgaatgaagc atttgttgtc     840
ccctatggga ctcctttggg tgtaaacttt ggtccgaccg tggatggtga tttttctcact    900
gacatgccag acatattact tgaacttgga caatttaaaa aaacccagat tttggtgggt     960
gttaataaag atgaagggac atggtttta gtcggtggtg ctcctggctt cagcaaagat    1020
aacaatagta tcataactag aaaagaattt caggaaggtt taaaaatatt ttttccagga    1080
gtgagtgagt ttggaaagga atccatcctt tttcattaca cagactgggt agatgatcag    1140
agacctgaaa actaccgtga ggccttgggt gatgttgttg gggattataa tttcatatgc    1200
cctgccttgg agttcaccaa gaagttctca gaatgggaa ataatgcctt tttctactat    1260
tttgaacacc gatcctccaa acttcgtgg ccagaatgga tgggagtgat gcatggctat    1320
gaaattgaat ttgtctttgg tttacctctg aaagaagag ataattacac aaaagccgag    1380
gaaattttga gtagatccat agtgaaacgg tgggcaaatt ttgcaaaata tgggaatcca    1440
aatgagactc agaacaatag cacaagctgg cctgtcttca aaagcactga acaaaaatat    1500
ctaaccttga atacagagtc aacaagaata atgacgaaac tacgtgctca acaatgtcga    1560
ttctggacat cattttttcc aaaagtcttg gaaatgacag gaaatattga tgaagcagaa    1620
tgggagtgga aagcaggatt ccatcgctgg aacaattaca tgatggactg gaaaaatcaa    1680
tttaacgatt acactagcaa gaaagaaagt tgtgtgggtc tc                       1722
```

<210> SEQ ID NO 18
<211> LENGTH: 574
<212> TYPE: PRT
<213> ORGANISM: Artificial Sequence
<220> FEATURE:
<223> OTHER INFORMATION: mutant of human BChE

<400> SEQUENCE: 18

Glu Asp Asp Ile Ile Ile Ala Thr Lys Asn Gly Lys Val Arg Gly Met
1               5                   10                  15

Asn Leu Thr Val Phe Gly Gly Thr Val Thr Ala Phe Leu Gly Ile Pro
            20                  25                  30

Tyr Ala Gln Pro Pro Leu Gly Arg Leu Arg Phe Lys Lys Pro Gln Ser
        35                  40                  45

Leu Thr Lys Trp Ser Asp Ile Trp Asn Ala Thr Lys Tyr Ala Asn Ser

-continued

```
            50                  55                  60
Cys Cys Gln Asn Ile Asp Gln Ser Phe Pro Gly Phe His Gly Ser Glu
 65                  70                  75                  80
Met Trp Asn Pro Asn Thr Asp Leu Ser Glu Asp Cys Leu Tyr Leu Asn
                 85                  90                  95
Val Trp Ile Pro Ala Pro Lys Pro Lys Asn Ala Thr Val Leu Ile Trp
                100                 105                 110
Ile Tyr Gly Gly Gly Phe Gln Thr Gly Thr Ser Ser Leu His Val Tyr
                115                 120                 125
Asp Gly Lys Phe Leu Ala Arg Val Glu Arg Val Ile Val Val Ser Met
130                 135                 140
Asn Tyr Arg Val Gly Ala Leu Gly Phe Leu Ala Leu Pro Gly Asn Pro
145                 150                 155                 160
Glu Ala Pro Gly Asn Met Gly Leu Phe Asp Gln Gln Leu Ala Leu Gln
                165                 170                 175
Trp Val Gln Lys Asn Ile Ala Ala Phe Gly Gly Asn Pro Lys Ser Val
                180                 185                 190
Thr Leu Phe Gly Glu Ser Ser Gly Ala Ala Ser Val Ser Leu His Leu
                195                 200                 205
Leu Ser Pro Gly Ser His Ser Leu Phe Thr Arg Ala Ile Leu Gln Ser
                210                 215                 220
Gly Ser Gly Asn Ala Pro Trp Ala Val Thr Ser Leu Tyr Glu Ala Arg
225                 230                 235                 240
Asn Arg Thr Leu Asn Leu Ala Lys Leu Thr Gly Cys Ser Arg Glu Asn
                245                 250                 255
Glu Thr Glu Ile Ile Lys Cys Leu Arg Asn Lys Asp Pro Gln Glu Ile
                260                 265                 270
Leu Leu Asn Glu Ala Phe Val Val Pro Tyr Gly Thr Pro Leu Gly Val
                275                 280                 285
Asn Phe Gly Pro Thr Val Asp Gly Asp Phe Leu Thr Asp Met Pro Asp
                290                 295                 300
Ile Leu Leu Glu Leu Gly Gln Phe Lys Lys Thr Gln Ile Leu Val Gly
305                 310                 315                 320
Val Asn Lys Asp Glu Gly Thr Trp Phe Leu Val Gly Gly Ala Pro Gly
                325                 330                 335
Phe Ser Lys Asp Asn Asn Ser Ile Ile Thr Arg Lys Glu Phe Gln Glu
                340                 345                 350
Gly Leu Lys Ile Phe Phe Pro Gly Val Ser Glu Phe Gly Lys Glu Ser
                355                 360                 365
Ile Leu Phe His Tyr Thr Asp Trp Val Asp Asp Gln Arg Pro Glu Asn
                370                 375                 380
Tyr Arg Glu Ala Leu Gly Asp Val Val Gly Asp Tyr Asn Phe Ile Cys
385                 390                 395                 400
Pro Ala Leu Glu Phe Thr Lys Lys Phe Ser Glu Trp Gly Asn Asn Ala
                405                 410                 415
Phe Phe Tyr Tyr Phe Glu His Arg Ser Ser Lys Leu Pro Trp Pro Glu
                420                 425                 430
Trp Met Gly Val Met His Gly Tyr Glu Ile Glu Phe Val Phe Gly Leu
                435                 440                 445
Pro Leu Glu Arg Arg Asp Asn Tyr Thr Lys Ala Glu Glu Ile Leu Ser
                450                 455                 460
Arg Ser Ile Val Lys Arg Trp Ala Asn Phe Ala Lys Tyr Gly Asn Pro
465                 470                 475                 480
```

Asn Glu Thr Gln Asn Asn Ser Thr Ser Trp Pro Val Phe Lys Ser Thr
              485                 490                 495

Glu Gln Lys Tyr Leu Thr Leu Asn Thr Glu Ser Thr Arg Ile Met Thr
          500                 505                 510

Lys Leu Arg Ala Gln Gln Cys Arg Phe Trp Thr Ser Phe Phe Pro Lys
      515                 520                 525

Val Leu Glu Met Thr Gly Asn Ile Asp Glu Ala Glu Trp Glu Trp Lys
  530                 535                 540

Ala Gly Phe His Arg Trp Asn Asn Tyr Met Met Asp Trp Lys Asn Gln
545             550                 555                 560

Phe Asn Asp Tyr Thr Ser Lys Lys Glu Ser Cys Val Gly Leu
              565                 570

<210> SEQ ID NO 19
<211> LENGTH: 1722
<212> TYPE: DNA
<213> ORGANISM: Artificial Sequence
<220> FEATURE:
<223> OTHER INFORMATION: mutant of human BChE

<400> SEQUENCE: 19
gaagatgaca tcataattgc aacaaagaat ggaaaagtca gagggatgaa cttgacagtt      60
tttggtggca cggtaacagc ctttcttgga attccctatg cacagccacc tcttggtaga     120
cttcgattca aaaagccaca gtctctgacc aagtggtctg atatttggaa tgccacaaaa     180
tatgcaaatt cttgctgtca gaacatagat caaagttttc caggcttcca tggatcagag     240
atgtggaacc caaacactga cctcagtgaa gactgtttat atctaaatgt atggattcca     300
gcacctaaac caaaaaatgc cactgtattg atatggattt atggtggtgg ttttcaaact     360
ggaacatcat ctttacatgt ttatgatggc aagtttctgg ctcgggttga agagttatt      420
gtagtgtcaa tgaactatag ggtgggtgcc ctaggattct tagctttgcc aggaaatcct     480
gaggctccag ggaacatggg tttatttgat caacagttgg ctcttcagtg ggttcaaaaa     540
aatatagcag cctttggtgg aaatcctaaa agtgtaactc tctttggaga agttccggg     600
gcagcttcag ttagcctgca tttgctttct cctggaagcc attcattgtt caccagagcc     660
attctgcaaa gtggttcctt taatgctcct tgggcggtaa catctctttta tgaagctagg     720
aacagaacgt tgaacttagc taaattgact ggttgctcta gagagaatga gactgaaata     780
atcaagtgtc ttagaaataa agatccccaa gaaattcttc tgaatgaagc atttgttgtc     840
ccctatggga cttccttggg tgtaaacttt ggtccgaccg tggatggtga ttttctcact     900
gacatgccag acatattact tgaacttgga caatttaaaa aacccagat tttggtgggt     960
gttaataaag atgaagggac atggttttta gtcggtggtg ctcctggctt cagcaaagat    1020
aacaatagta tcataactag aaaagaattt caggaaggtt taaaaatatt ttttccagga    1080
gtgagtgagt ttggaaagga atccatcctt tttcattaca cagactgggt agatgatcag    1140
agacctgaaa actaccgtga ggccttgggt gatgttgttg gggattataa tttcatatgc    1200
cctgccttgg agttcaccaa gaagttctca gaatgggaa ataatgcctt tttctactat    1260
tttgaacacc gatcctccaa acttccgtgg ccagaatgga tgggagtgat gcatggctat    1320
gaaattgaat ttgtctttgg tttacctctg gaaagaagag ataattacac aaaagccgag    1380
gaaattttga gtagatccat agtgaaacgg tgggcaaatt ttgcaaaata tgggaatcca    1440
aatgagactc agaacaatag cacaagctgg cctgtcttca aaagcactga acaaaaatat    1500

```
ctaaccttga atacagagtc aacaagaata atgacgaaac tacgtgctca acaatgtcga    1560
ttctggacat catttttttcc aaaagtcttg gaaatgacag gaaatattga tgaagcagaa   1620
tgggagtgga aagcaggatt ccatcgctgg aacaattaca tgatggactg gaaaaatcaa   1680
tttaacgatt acactagcaa gaaagaaagt tgtgtgggtc tc                      1722
```

<210> SEQ ID NO 20
<211> LENGTH: 574
<212> TYPE: PRT
<213> ORGANISM: Artificial Sequence
<220> FEATURE:
<223> OTHER INFORMATION: mutant of human BChE

<400> SEQUENCE: 20

| | | | | | | | | | | | | | | |
|---|---|---|---|---|---|---|---|---|---|---|---|---|---|---|
| Glu | Asp | Asp | Ile | Ile | Ile | Ala | Thr | Lys | Asn | Gly | Lys | Val | Arg | Gly |
| 1 | | | | 5 | | | | | 10 | | | | | 15 |
| Met Asn Leu Thr Val Phe Gly Gly Thr Val Thr Ala Phe Leu Gly Ile Pro |

Asn Leu Thr Val Phe Gly Gly Thr Val Thr Ala Phe Leu Gly Ile Pro
            20                  25                  30

Tyr Ala Gln Pro Pro Leu Gly Arg Leu Arg Phe Lys Lys Pro Gln Ser
        35                  40                  45

Leu Thr Lys Trp Ser Asp Ile Trp Asn Ala Thr Lys Tyr Ala Asn Ser
 50                  55                  60

Cys Cys Gln Asn Ile Asp Gln Ser Phe Pro Gly Phe His Gly Ser Glu
65                  70                  75                  80

Met Trp Asn Pro Asn Thr Asp Leu Ser Glu Asp Cys Leu Tyr Leu Asn
                85                  90                  95

Val Trp Ile Pro Ala Pro Lys Pro Lys Asn Ala Thr Val Leu Ile Trp
            100                 105                 110

Ile Tyr Gly Gly Gly Phe Gln Thr Gly Thr Ser Ser Leu His Val Tyr
        115                 120                 125

Asp Gly Lys Phe Leu Ala Arg Val Glu Arg Val Ile Val Val Ser Met
130                 135                 140

Asn Tyr Arg Val Gly Ala Leu Gly Phe Leu Ala Leu Pro Gly Asn Pro
145                 150                 155                 160

Glu Ala Pro Gly Asn Met Gly Leu Phe Asp Gln Gln Leu Ala Leu Gln
                165                 170                 175

Trp Val Gln Lys Asn Ile Ala Ala Phe Gly Gly Asn Pro Lys Ser Val
            180                 185                 190

Thr Leu Phe Gly Glu Ser Ser Gly Ala Ala Ser Val Ser Leu His Leu
        195                 200                 205

Leu Ser Pro Gly Ser His Ser Leu Phe Thr Arg Ala Ile Leu Gln Ser
210                 215                 220

Gly Ser Phe Asn Ala Pro Trp Ala Val Thr Ser Leu Tyr Glu Ala Arg
225                 230                 235                 240

Asn Arg Thr Leu Asn Leu Ala Lys Leu Thr Gly Cys Ser Arg Glu Asn
                245                 250                 255

Glu Thr Glu Ile Ile Lys Cys Leu Arg Asn Lys Asp Pro Gln Glu Ile
            260                 265                 270

Leu Leu Asn Glu Ala Phe Val Val Pro Tyr Gly Thr Ser Leu Gly Val
        275                 280                 285

Asn Phe Gly Pro Thr Val Asp Gly Asp Phe Leu Thr Asp Met Pro Asp
290                 295                 300

Ile Leu Leu Glu Leu Gly Gln Phe Lys Lys Thr Gln Ile Leu Val Gly
305                 310                 315                 320

Val Asn Lys Asp Glu Gly Thr Trp Phe Leu Val Gly Gly Ala Pro Gly

```
                    325                 330                 335
Phe Ser Lys Asp Asn Asn Ser Ile Ile Thr Arg Lys Glu Phe Gln Glu
            340                 345                 350
Gly Leu Lys Ile Phe Phe Pro Gly Val Ser Glu Phe Gly Lys Glu Ser
            355                 360                 365
Ile Leu Phe His Tyr Thr Asp Trp Val Asp Asp Gln Arg Pro Glu Asn
            370                 375                 380
Tyr Arg Glu Ala Leu Gly Asp Val Val Gly Asp Tyr Asn Phe Ile Cys
385                 390                 395                 400
Pro Ala Leu Glu Phe Thr Lys Lys Phe Ser Glu Trp Gly Asn Asn Ala
            405                 410                 415
Phe Phe Tyr Tyr Phe Glu His Arg Ser Ser Lys Leu Pro Trp Pro Glu
            420                 425                 430
Trp Met Gly Val Met His Gly Tyr Glu Ile Glu Phe Val Phe Gly Leu
            435                 440                 445
Pro Leu Glu Arg Arg Asp Asn Tyr Thr Lys Ala Glu Glu Ile Leu Ser
            450                 455                 460
Arg Ser Ile Val Lys Arg Trp Ala Asn Phe Ala Lys Tyr Gly Asn Pro
465                 470                 475                 480
Asn Glu Thr Gln Asn Asn Ser Thr Ser Trp Pro Val Phe Lys Ser Thr
            485                 490                 495
Glu Gln Lys Tyr Leu Thr Leu Asn Thr Glu Ser Thr Arg Ile Met Thr
            500                 505                 510
Lys Leu Arg Ala Gln Gln Cys Arg Phe Trp Thr Ser Phe Phe Pro Lys
            515                 520                 525
Val Leu Glu Met Thr Gly Asn Ile Asp Glu Ala Glu Trp Glu Trp Lys
            530                 535                 540
Ala Gly Phe His Arg Trp Asn Asn Tyr Met Met Asp Trp Lys Asn Gln
545                 550                 555                 560
Phe Asn Asp Tyr Thr Ser Lys Lys Glu Ser Cys Val Gly Leu
            565                 570
```

<210> SEQ ID NO 21
<211> LENGTH: 1722
<212> TYPE: DNA
<213> ORGANISM: Artificial Sequence
<220> FEATURE:
<223> OTHER INFORMATION: mutant of human BChE

<400> SEQUENCE: 21

```
gaagatgaca tcataattgc aacaaagaat ggaaaagtca gagggatgaa cttgacagtt     60
tttggtggca cggtaacagc ctttcttgga attccctatg cacagccacc tcttggtaga    120
cttcgattca aaaagccaca gtctctgacc aagtggtctg atatttggaa tgccacaaaa    180
tatgcaaatt cttgctgtca gaacatagat caaagttttc caggcttcca tggatcagag    240
atgtggaacc caaacactga cctcagtgaa gactgtttat atctaaatgt atggattcca    300
gcacctaaac caaaaaatgc cactgtattg atatggattt atggtggtgg ttttcaaact    360
ggaacatcat ctttacatgt ttatgatggc aagtttctgg ctcgggttga agagttatt     420
gtagtgtcaa tgaactatag ggtgggtgcc taggattct tagctttgcc aggaaatcct     480
gaggctccag ggaacatggg tttatttgat caacagttgg ctcttcagtg ggttcaaaaa    540
aatatagcag cctttggtgg aaatcctaaa agtgtaactc tctttggaga aagttccgga    600
gcagcttcag ttagcctgca tttgctttct cctggaagcc attcattgtt caccagagcc    660
```

-continued

```
attctgcaaa gtggttccgt taatgctcct tgggcggtaa catctcttta tgaagctagg    720
aacagaacgt tgaacttagc taaattgact ggttgctcta gagagaatga gactgaaata    780
atcaagtgtc ttagaaataa agatccccaa gaaattcttc tgaatgaagc atttgttgtc    840
ccctatggga ctcctttggg tgtaaacttt ggtccgaccg tggatggtga ttttctcact    900
gacatgccag acatattact tgaacttgga caatttaaaa aaacccagat tttggtgggt    960
gttaataaag atgaagggac atggttttta gtcggtggtg ctcctggctt cagcaaagat   1020
aacaatagta tcataactag aaaagaattt caggaaggtt taaaaatatt ttttccagga   1080
gtgagtgagt ttggaaagga atccatcctt tttcattaca cagactgggt agatgatcag   1140
agacctgaaa actaccgtga ggccttgggt gatgttgttg gggattataa tttcatatgc   1200
cctgccttgg agttcaccaa gaagttctca gaatggggaa ataatgcctt tttctactat   1260
tttgaacacc gatcctccaa acttccgtgg ccagaatgga tgggagtgat gcatggctat   1320
gaaattgaat ttgtctttgg tttacctctg gaaagaagag ataattacac aaaagccgag   1380
gaaattttga gtagatccat agtgaaacgg tgggcaaatt ttgcaaaata tgggaatcca   1440
aatgagactc agaacaatag cacaagctgg cctgtcttca aaagcactga acaaaaatat   1500
ctaaccttga atacagagtc aacaagaata atgacgaaac tacgtgctca acaatgtcga   1560
ttctggacat cattttttcc aaaagtcttg gaaatgacag aaatattga tgaagcagaa   1620
tgggagtgga agcaggatt ccatcgctgg aacaattaca tgatggactg gaaaaatcaa   1680
tttaacgatt acactagcaa gaaagaaagt tgtgtgggtc tc                      1722
```

<210> SEQ ID NO 22
<211> LENGTH: 574
<212> TYPE: PRT
<213> ORGANISM: Artificial Sequence
<220> FEATURE:
<223> OTHER INFORMATION: mutant of human BChE

<400> SEQUENCE: 22

```
Glu Asp Asp Ile Ile Ile Ala Thr Lys Asn Gly Lys Val Arg Gly Met
1               5                   10                  15

Asn Leu Thr Val Phe Gly Gly Thr Val Thr Ala Phe Leu Gly Ile Pro
            20                  25                  30

Tyr Ala Gln Pro Pro Leu Gly Arg Leu Arg Phe Lys Lys Pro Gln Ser
        35                  40                  45

Leu Thr Lys Trp Ser Asp Ile Trp Asn Ala Thr Lys Tyr Ala Asn Ser
    50                  55                  60

Cys Cys Gln Asn Ile Asp Gln Ser Phe Pro Gly Phe His Gly Ser Glu
65                  70                  75                  80

Met Trp Asn Pro Asn Thr Asp Leu Ser Glu Asp Cys Leu Tyr Leu Asn
                85                  90                  95

Val Trp Ile Pro Ala Pro Lys Pro Lys Asn Ala Thr Val Leu Ile Trp
            100                 105                 110

Ile Tyr Gly Gly Gly Phe Gln Thr Gly Thr Ser Ser Leu His Val Tyr
        115                 120                 125

Asp Gly Lys Phe Leu Ala Arg Val Glu Arg Val Ile Val Val Ser Met
    130                 135                 140

Asn Tyr Arg Val Gly Ala Leu Gly Phe Leu Ala Leu Pro Gly Asn Pro
145                 150                 155                 160

Glu Ala Pro Gly Asn Met Gly Leu Phe Asp Gln Gln Leu Ala Leu Gln
                165                 170                 175
```

-continued

```
Trp Val Gln Lys Asn Ile Ala Ala Phe Gly Asn Pro Lys Ser Val
            180                 185                 190

Thr Leu Phe Gly Glu Ser Ser Gly Ala Ala Ser Val Ser Leu His Leu
        195                 200                 205

Leu Ser Pro Gly Ser His Ser Leu Phe Thr Arg Ala Ile Leu Gln Ser
    210                 215                 220

Gly Ser Val Asn Ala Pro Trp Ala Val Thr Ser Leu Tyr Glu Ala Arg
225                 230                 235                 240

Asn Arg Thr Leu Asn Leu Ala Lys Leu Thr Gly Cys Ser Arg Glu Asn
                245                 250                 255

Glu Thr Glu Ile Ile Lys Cys Leu Arg Asn Lys Asp Pro Gln Glu Ile
            260                 265                 270

Leu Leu Asn Glu Ala Phe Val Val Pro Tyr Gly Thr Pro Leu Gly Val
        275                 280                 285

Asn Phe Gly Pro Thr Val Asp Gly Asp Phe Leu Thr Asp Met Pro Asp
    290                 295                 300

Ile Leu Leu Glu Leu Gly Gln Phe Lys Lys Thr Gln Ile Leu Val Gly
305                 310                 315                 320

Val Asn Lys Asp Glu Gly Thr Trp Phe Leu Val Gly Gly Ala Pro Gly
                325                 330                 335

Phe Ser Lys Asp Asn Asn Ser Ile Ile Thr Arg Lys Glu Phe Gln Glu
            340                 345                 350

Gly Leu Lys Ile Phe Phe Pro Gly Val Ser Glu Phe Gly Lys Glu Ser
        355                 360                 365

Ile Leu Phe His Tyr Thr Asp Trp Val Asp Asp Gln Arg Pro Glu Asn
    370                 375                 380

Tyr Arg Glu Ala Leu Gly Asp Val Val Gly Asp Tyr Asn Phe Ile Cys
385                 390                 395                 400

Pro Ala Leu Glu Phe Thr Lys Lys Phe Ser Glu Trp Gly Asn Asn Ala
                405                 410                 415

Phe Phe Tyr Tyr Phe Glu His Arg Ser Ser Lys Leu Pro Trp Pro Glu
            420                 425                 430

Trp Met Gly Val Met His Gly Tyr Glu Ile Glu Phe Val Phe Gly Leu
        435                 440                 445

Pro Leu Glu Arg Arg Asp Asn Tyr Thr Lys Ala Glu Glu Ile Leu Ser
    450                 455                 460

Arg Ser Ile Val Lys Arg Trp Ala Asn Phe Ala Lys Tyr Gly Asn Pro
465                 470                 475                 480

Asn Glu Thr Gln Asn Asn Ser Thr Ser Trp Pro Val Phe Lys Ser Thr
                485                 490                 495

Glu Gln Lys Tyr Leu Thr Leu Asn Thr Glu Ser Thr Arg Ile Met Thr
            500                 505                 510

Lys Leu Arg Ala Gln Gln Cys Arg Phe Trp Thr Ser Phe Phe Pro Lys
        515                 520                 525

Val Leu Glu Met Thr Gly Asn Ile Asp Glu Ala Glu Trp Glu Trp Lys
    530                 535                 540

Ala Gly Phe His Arg Trp Asn Asn Tyr Met Met Asp Trp Lys Asn Gln
545                 550                 555                 560

Phe Asn Asp Tyr Thr Ser Lys Lys Glu Ser Cys Val Gly Leu
                565                 570
```

<210> SEQ ID NO 23
<211> LENGTH: 1722
<212> TYPE: DNA

<213> ORGANISM: Artificial Sequence
<220> FEATURE:
<223> OTHER INFORMATION: mutant of human BChE

<400> SEQUENCE: 23

```
gaagatgaca tcataattgc aacaaagaat ggaaaagtca gagggatgaa cttgacagtt      60
tttggtggca cggtaacagc ctttcttgga attccctatg cacagccacc tcttggtaga     120
cttcgattca aaaagccaca gtctctgacc aagtggtctg atatttggaa tgccacaaaa     180
tatgcaaatt cttgctgtca aacatagat caaagttttc aggcttcca tggatcagag      240
atgtggaacc caaacactga cctcagtgaa gactgtttat atctaaatgt atggattcca     300
gcacctaaac caaaaatgc cactgtattg atatggattt atggtggtgg ttttcaaact     360
ggaacatcat ctttacatgt ttatgatggc aagtttctgg ctcgggttga agagttatt      420
gtagtgtcaa tgaactatag ggtgggtgcc ctaggattct tagctttgcc aggaaatcct     480
gaggctccag ggaacatggg tttatttgat aacagttgg ctcttcagtg ggttcaaaaa      540
aatatagcag cctttggtgg aaatcctaaa agtgtaactc tctttggaga agttccgga     600
gcagcttcag ttagcctgca tttgctttct cctggaagcc attcattgtt caccagagcc    660
attctgcaaa gtggttcctt taatgctcct tgggcggtaa catctcttta tgaagctagg    720
aacagaacgt tgaacttagc taaattgact ggttgctcta gagagaatga gactgaaata    780
atcaagtgtc ttagaaataa agatccccaa gaaattcttc tgaatgaagc atttgttgtc    840
ccctatggga ctggtttggg tgtaaacttt ggtccgaccg tggatggtga ttttctcact    900
gacatgccag acatattact tgaacttgga caatttaaaa aacccagat tttggtgggt     960
gttaataaag atgaagggac atggttttta gtcggtggtg ctcctggctt cagcaaagat   1020
aacaatagta tcataactag aaaagaattt caggaaggtt taaaaatatt ttttccagga   1080
gtgagtgagt ttgaaaagga atccatcctt tttcattaca cagactgggt agatgatcag   1140
agacctgaaa actaccgtga ggccttgggt gatgttgttg gggattataa tttcatatgc   1200
cctgccttgg agttcaccaa gaagttctca gaatggggaa ataatgcctt tttctactat   1260
tttgaacacc gatcctccaa acttccgtgg ccagaatgga tgggagtgat gcatggctat   1320
gaaattgaat tgtctttgg tttacctctg gaaagaagag ataattacac aaaagccgag   1380
gaaattttga gtagatccat agtgaaacgg tgggcaaatt ttgcaaaata tgggaatcca   1440
aatgagactc agaacaatag cacaagctgg cctgtcttca aaagcactga acaaaaatat   1500
ctaaccttga atacagagtc aacaagaata atgacgaaac tacgtgctca acaatgtcga   1560
ttctggacat cattttttcc aaaagtcttg gaaatgacag aaatattga tgaagcagaa   1620
tgggagtgga aagcaggatt ccatcgctgg aacaattaca tgatggactg gaaaaatcaa   1680
tttaacgatt acactagcaa gaaagaaagt tgtgtgggtc tc                      1722
```

<210> SEQ ID NO 24
<211> LENGTH: 574
<212> TYPE: PRT
<213> ORGANISM: Artificial Sequence
<220> FEATURE:
<223> OTHER INFORMATION: mutant of human BChE

<400> SEQUENCE: 24

```
Glu Asp Asp Ile Ile Ile Ala Thr Lys Asn Gly Lys Val Arg Gly Met
1               5                   10                  15

Asn Leu Thr Val Phe Gly Gly Thr Val Thr Ala Phe Leu Gly Ile Pro
            20                  25                  30
```

```
Tyr Ala Gln Pro Pro Leu Gly Arg Leu Arg Phe Lys Lys Pro Gln Ser
        35                  40                  45

Leu Thr Lys Trp Ser Asp Ile Trp Asn Ala Thr Lys Tyr Ala Asn Ser
    50                  55                  60

Cys Cys Gln Asn Ile Asp Gln Ser Phe Pro Gly Phe His Gly Ser Glu
65                  70                  75                  80

Met Trp Asn Pro Asn Thr Asp Leu Ser Glu Asp Cys Leu Tyr Leu Asn
                85                  90                  95

Val Trp Ile Pro Ala Pro Lys Pro Lys Asn Ala Thr Val Leu Ile Trp
                100                 105                 110

Ile Tyr Gly Gly Gly Phe Gln Thr Gly Thr Ser Ser Leu His Val Tyr
                115                 120                 125

Asp Gly Lys Phe Leu Ala Arg Val Glu Arg Val Ile Val Val Ser Met
    130                 135                 140

Asn Tyr Arg Val Gly Ala Leu Gly Phe Leu Ala Leu Pro Gly Asn Pro
145                 150                 155                 160

Glu Ala Pro Gly Asn Met Gly Leu Phe Asp Gln Gln Leu Ala Leu Gln
                165                 170                 175

Trp Val Gln Lys Asn Ile Ala Ala Phe Gly Gly Asn Pro Lys Ser Val
                180                 185                 190

Thr Leu Phe Gly Glu Ser Ser Gly Ala Ala Ser Val Ser Leu His Leu
                195                 200                 205

Leu Ser Pro Gly Ser His Ser Leu Phe Thr Arg Ala Ile Leu Gln Ser
    210                 215                 220

Gly Ser Phe Asn Ala Pro Trp Ala Val Thr Ser Leu Tyr Glu Ala Arg
225                 230                 235                 240

Asn Arg Thr Leu Asn Leu Ala Lys Leu Thr Gly Cys Ser Arg Glu Asn
                245                 250                 255

Glu Thr Glu Ile Ile Lys Cys Leu Arg Asn Lys Asp Pro Gln Glu Ile
                260                 265                 270

Leu Leu Asn Glu Ala Phe Val Val Pro Tyr Gly Thr Gly Leu Gly Val
    275                 280                 285

Asn Phe Gly Pro Thr Val Asp Gly Asp Phe Leu Thr Asp Met Pro Asp
    290                 295                 300

Ile Leu Leu Glu Leu Gly Gln Phe Lys Lys Thr Gln Ile Leu Val Gly
305                 310                 315                 320

Val Asn Lys Asp Glu Gly Thr Trp Phe Leu Val Gly Gly Ala Pro Gly
                325                 330                 335

Phe Ser Lys Asp Asn Asn Ser Ile Ile Thr Arg Lys Glu Phe Gln Glu
                340                 345                 350

Gly Leu Lys Ile Phe Phe Pro Gly Val Ser Glu Phe Gly Lys Glu Ser
    355                 360                 365

Ile Leu Phe His Tyr Thr Asp Trp Val Asp Gln Arg Pro Glu Asn
    370                 375                 380

Tyr Arg Glu Ala Leu Gly Asp Val Val Gly Asp Tyr Asn Phe Ile Cys
385                 390                 395                 400

Pro Ala Leu Glu Phe Thr Lys Lys Phe Ser Glu Trp Gly Asn Asn Ala
                405                 410                 415

Phe Phe Tyr Tyr Phe Glu His Arg Ser Ser Lys Leu Pro Trp Pro Glu
                420                 425                 430

Trp Met Gly Val Met His Gly Tyr Glu Ile Glu Phe Val Phe Gly Leu
    435                 440                 445
```

```
Pro Leu Glu Arg Arg Asp Asn Tyr Thr Lys Ala Glu Glu Ile Leu Ser
    450                 455                 460
Arg Ser Ile Val Lys Arg Trp Ala Asn Phe Ala Lys Tyr Gly Asn Pro
465                 470                 475                 480
Asn Glu Thr Gln Asn Asn Ser Thr Ser Trp Pro Val Phe Lys Ser Thr
                485                 490                 495
Glu Gln Lys Tyr Leu Thr Leu Asn Thr Glu Ser Thr Arg Ile Met Thr
            500                 505                 510
Lys Leu Arg Ala Gln Gln Cys Arg Phe Trp Thr Ser Phe Phe Pro Lys
        515                 520                 525
Val Leu Glu Met Thr Gly Asn Ile Asp Glu Ala Glu Trp Glu Trp Lys
    530                 535                 540
Ala Gly Phe His Arg Trp Asn Asn Tyr Met Met Asp Trp Lys Asn Gln
545                 550                 555                 560
Phe Asn Asp Tyr Thr Ser Lys Lys Glu Ser Cys Val Gly Leu
                565                 570
```

<210> SEQ ID NO 25
<211> LENGTH: 1722
<212> TYPE: DNA
<213> ORGANISM: Artificial Sequence
<220> FEATURE:
<223> OTHER INFORMATION: mutant of human BChE

<400> SEQUENCE: 25

| | | | | | |
|---|---|---|---|---|---|
| gaagatgaca | tcataattgc | aacaaagaat | ggaaaagtca | gagggatgaa | cttgacagtt | 60 |
| tttggtggca | cggtaacagc | cttkcttgga | attccctatg | cacagccacc | tcttggtaga | 120 |
| cttcgattca | aaaagccaca | gtctctgacc | aagtggtctg | atatttggaa | tgccacaaaa | 180 |
| tatgcaaatt | cttgctgtca | gaacatagat | caaagttttc | caggcttcca | tggatcagag | 240 |
| atgtggaacc | caaacactga | cctcagtgaa | gactgtttat | atctaaatgt | atggattcca | 300 |
| gcacctaaac | caaaaaatgc | cactgtattg | atatggattt | atggtggtgg | ttttcaaact | 360 |
| ggaacatcat | ctttacatgt | ttatgatggc | aagtttctgg | ctcgggttga | aagagttatt | 420 |
| gtagtgtcaa | tgaactatag | ggtgggtgcc | ctaggattct | tagctttgcc | aggaaatcct | 480 |
| gaggctccag | ggaacatggg | tttatttgat | caacagttgg | ctcttcagtg | ggttcaaaaa | 540 |
| aatatagcag | cctttggtgg | aaatcctaaa | agtgtaactc | tctttggaga | aagttccgga | 600 |
| gcagcttcag | ttagcctgca | tttgctttct | cctggaagcc | attcattgtt | caccagagcc | 660 |
| attctgcaaa | gtggttccat | caatgctcct | tgggcggtaa | catctcttta | tgaagctagg | 720 |
| aacagaacgt | tgaacttagc | taaattgact | ggttgctcta | gagagaatga | gactgaaata | 780 |
| atcaagtgtc | ttagaaataa | agatccccaa | gaaattcttc | tgaatgaagc | atttgttgtc | 840 |
| ccctatggga | ctccttggg | tgtaaacttt | ggtccgaccg | tggatggtga | ttttctcact | 900 |
| gacatgccag | acatattact | tgaacttgga | caatttaaaa | aaacccagat | tttgtgggt | 960 |
| gttaataaag | atgaagggac | atggtttta | gtcggtggtg | ctcctggctt | cagcaaagat | 1020 |
| aacaatagta | tcataactag | aaaagaattt | caggaaggtt | taaaaatatt | ttttccagga | 1080 |
| gtgagtgagt | ttggaaagga | atccatcctt | tttcattaca | cagactgggt | agatgatcag | 1140 |
| agacctgaaa | actaccgtga | ggcctggggt | gatgttgttg | gggattataa | tttcatatgc | 1200 |
| cctgccttgg | agttcaccaa | gaagttctca | gaatgggaa | ataatgcctt | tttctactat | 1260 |
| tttgaacacc | gatcctccaa | acttccgtgg | ccagaatgga | tgggagtgat | gcatggctat | 1320 |
| gaaattgaat | ttgtctttgg | tttacctctg | gaaagaagag | ataattacac | aaaagccgag | 1380 |

```
gaaattttga gtagatccat agtgaaacgg tgggcaaatt ttgcaaaata tgggaatcca    1440
aatgagactc agaacaatag cacaagctgg cctgtcttca aaagcactga acaaaaatat    1500
ctaaccttga atacagagtc aacaagaata atgacgaaac tacgtgctca acaatgtcga    1560
ttctggacat cattttttcc aaaagtcttg gaaatgacag gaaatattga tgaagcagaa    1620
tgggagtgga agcaggatt ccatcgctgg aacaattaca tgatggactg gaaaaatcaa    1680
tttaacgatt acactagcaa gaaagaaagt tgtgtgggtc tc                      1722
```

<210> SEQ ID NO 26
<211> LENGTH: 574
<212> TYPE: PRT
<213> ORGANISM: Artificial Sequence
<220> FEATURE:
<223> OTHER INFORMATION: mutant of human BChE

<400> SEQUENCE: 26

```
Glu Asp Asp Ile Ile Ile Ala Thr Lys Asn Gly Lys Val Arg Gly Met
1               5                   10                  15

Asn Leu Thr Val Phe Gly Gly Thr Val Thr Ala Phe Leu Gly Ile Pro
            20                  25                  30

Tyr Ala Gln Pro Pro Leu Gly Arg Leu Arg Phe Lys Lys Pro Gln Ser
        35                  40                  45

Leu Thr Lys Trp Ser Asp Ile Trp Asn Ala Thr Lys Tyr Ala Asn Ser
    50                  55                  60

Cys Cys Gln Asn Ile Asp Gln Ser Phe Pro Gly Phe His Gly Ser Glu
65                  70                  75                  80

Met Trp Asn Pro Asn Thr Asp Leu Ser Glu Asp Cys Leu Tyr Leu Asn
                85                  90                  95

Val Trp Ile Pro Ala Pro Lys Pro Lys Asn Ala Thr Val Leu Ile Trp
            100                 105                 110

Ile Tyr Gly Gly Gly Phe Gln Thr Gly Thr Ser Ser Leu His Val Tyr
        115                 120                 125

Asp Gly Lys Phe Leu Ala Arg Val Glu Arg Val Ile Val Val Ser Met
    130                 135                 140

Asn Tyr Arg Val Gly Ala Leu Gly Phe Leu Ala Leu Pro Gly Asn Pro
145                 150                 155                 160

Glu Ala Pro Gly Asn Met Gly Leu Phe Asp Gln Gln Leu Ala Leu Gln
                165                 170                 175

Trp Val Gln Lys Asn Ile Ala Ala Phe Gly Gly Asn Pro Lys Ser Val
            180                 185                 190

Thr Leu Phe Gly Glu Ser Ser Gly Ala Ala Ser Val Ser Leu His Leu
        195                 200                 205

Leu Ser Pro Gly Ser His Ser Leu Phe Thr Arg Ala Ile Leu Gln Ser
    210                 215                 220

Gly Ser Ile Asn Ala Pro Trp Ala Val Thr Ser Leu Tyr Glu Ala Arg
225                 230                 235                 240

Asn Arg Thr Leu Asn Leu Ala Lys Leu Thr Gly Cys Ser Arg Glu Asn
                245                 250                 255

Glu Thr Glu Ile Ile Lys Cys Leu Arg Asn Lys Asp Pro Gln Glu Ile
            260                 265                 270

Leu Leu Asn Glu Ala Phe Val Val Pro Tyr Gly Thr Pro Leu Gly Val
        275                 280                 285

Asn Phe Gly Pro Thr Val Asp Gly Asp Phe Leu Thr Asp Met Pro Asp
    290                 295                 300
```

```
Ile Leu Leu Glu Leu Gly Gln Phe Lys Lys Thr Gln Ile Leu Val Gly
305                 310                 315                 320

Val Asn Lys Asp Glu Gly Thr Trp Phe Leu Val Gly Gly Ala Pro Gly
                325                 330                 335

Phe Ser Lys Asp Asn Asn Ser Ile Ile Thr Arg Lys Glu Phe Gln Glu
                340                 345                 350

Gly Leu Lys Ile Phe Phe Pro Gly Val Ser Glu Phe Lys Glu Ser
            355                 360                 365

Ile Leu Phe His Tyr Thr Asp Trp Val Asp Asp Gln Arg Pro Glu Asn
        370                 375                 380

Tyr Arg Glu Ala Leu Gly Asp Val Val Gly Asp Tyr Asn Phe Ile Cys
385                 390                 395                 400

Pro Ala Leu Glu Phe Thr Lys Lys Phe Ser Glu Trp Gly Asn Asn Ala
                405                 410                 415

Phe Phe Tyr Tyr Phe Glu His Arg Ser Ser Lys Leu Pro Trp Pro Glu
                420                 425                 430

Trp Met Gly Val Met His Gly Tyr Glu Ile Glu Phe Val Phe Gly Leu
            435                 440                 445

Pro Leu Glu Arg Arg Asp Asn Tyr Thr Lys Ala Glu Glu Ile Leu Ser
            450                 455                 460

Arg Ser Ile Val Lys Arg Trp Ala Asn Phe Ala Lys Tyr Gly Asn Pro
465                 470                 475                 480

Asn Glu Thr Gln Asn Asn Ser Thr Ser Trp Pro Val Phe Lys Ser Thr
                485                 490                 495

Glu Gln Lys Tyr Leu Thr Leu Asn Thr Glu Ser Thr Arg Ile Met Thr
            500                 505                 510

Lys Leu Arg Ala Gln Gln Cys Arg Phe Trp Thr Ser Phe Phe Pro Lys
        515                 520                 525

Val Leu Glu Met Thr Gly Asn Ile Asp Glu Ala Glu Trp Glu Trp Lys
    530                 535                 540

Ala Gly Phe His Arg Trp Asn Asn Tyr Met Met Asp Trp Lys Asn Gln
545                 550                 555                 560

Phe Asn Asp Tyr Thr Ser Lys Lys Glu Ser Cys Val Gly Leu
                565                 570

<210> SEQ ID NO 27
<211> LENGTH: 1722
<212> TYPE: DNA
<213> ORGANISM: Artificial Sequence
<220> FEATURE:
<223> OTHER INFORMATION: mutant of human BChE

<400> SEQUENCE: 27
gaagatgaca tcataattgc aacaaagaat ggaaaagtca gagggatgaa cttgacagtt      60
tttggtggca cggtaacagc cttttcttgga attccctatg cacagccacc tcttggtaga     120
cttcgattca aaaagccaca gtctctgacc aagtggtctg atatttggaa tgccacaaaa     180
tatgcaaatt cttgctgtca gaacatagat caaagtttc caggcttcca tggatcagag      240
atgtggaacc caaacactga cctcagtgaa gactgtttat atctaaatgt atggattcca     300
gcacctaaac caaaaaatgc cactgtattg atatggattt atggtggtgg tttttcaaact    360 ggaacatcat ctttacatgt ttatgatggc aagtttctgg ctcgggttga agagttatt      420 gtagtgtcaa tgaactatag ggtgggtgcc ctaggattct tagctttgcc aggaaatcct     480
gaggctccag ggaacatggg tttatttgat caacagttgg ctcttcagtg ggttcaaaaa     540
```

-continued

```
aatatagcag cctttggtgg aaatcctaaa agtgtaactc tctttggaga aagttccgga      600
gcagcttcag ttagcctgca tttgctttct cctggaagcc attcattgtt caccagagcc      660
attctgcaaa gtggttccct gaatgctcct tgggcggtaa catctcttta tgaagctagg      720
aacagaacgt tgaacttagc taaattgact ggttgctcta gagagaatga gactgaaata      780
atcaagtgtc ttagaaataa agatccccaa gaaattcttc tgaatgaagc atttgttgtc      840
ccctatggga ctcctttggg tgtaaacttt ggtccgaccg tggatggtga ttttctcact      900
gacatgccag acatattact tgaacttgga caatttaaaa aaacccagat tttggtgggt      960
gttaataaag atgaagggac atggttttta gtcggtggtg ctcctggctt cagcaaagat     1020
aacaatagta tcataactag aaaagaattt caggaaggtt taaaaatatt ttttccagga     1080
gtgagtgagt ttggaaagga atccatcctt tttcattaca cagactgggt agatgatcag     1140
agacctgaaa actaccgtga ggccttgggt gatgttgttg gggattataa tttcatatgc     1200
cctgccttgg agttcaccaa gaagttctca gaatgtggaa ataatgcctt tttctactat     1260
tttgaacacc gatcctccaa acttccgtgg ccagaatgga tgggagtgat gcatggctat     1320
gaaattgaat ttgtctttgg tttacctctg gaaagaagag ataattacac aaaagccgag     1380
gaaattttga gtagatccat agtgaaacgg tgggcaaatt ttgcaaaata tgggaatcca     1440
aatgagactc agaacaatag cacaagctgg cctgtcttca aaagcactga acaaaaatat     1500
ctaaccttga atacagagtc aacaagaata atgacgaaac tacgtgctca acaatgtcga     1560
ttctggacat cattttttcc aaaagtcttg gaaatgacag gaaatattga tgaagcagaa     1620
tgggagtgga aagcaggatt ccatcgctgg aacaattaca tgatggactg gaaaaatcaa     1680
tttaacgatt acactagcaa gaaagaaagt tgtgtgggtc tc                         1722
```

<210> SEQ ID NO 28
<211> LENGTH: 574
<212> TYPE: PRT
<213> ORGANISM: Artificial Sequence
<220> FEATURE:
<223> OTHER INFORMATION: mutant of human BChE

<400> SEQUENCE: 28

```
Glu Asp Asp Ile Ile Ile Ala Thr Lys Asn Gly Lys Val Arg Gly Met
1               5                   10                  15

Asn Leu Thr Val Phe Gly Gly Thr Val Thr Ala Phe Leu Gly Ile Pro
            20                  25                  30

Tyr Ala Gln Pro Pro Leu Gly Arg Leu Arg Phe Lys Lys Pro Gln Ser
        35                  40                  45

Leu Thr Lys Trp Ser Asp Ile Trp Asn Ala Thr Lys Tyr Ala Asn Ser
    50                  55                  60

Cys Cys Gln Asn Ile Asp Gln Ser Phe Pro Gly Phe His Gly Ser Glu
65                  70                  75                  80

Met Trp Asn Pro Asn Thr Asp Leu Ser Glu Asp Cys Leu Tyr Leu Asn
                85                  90                  95

Val Trp Ile Pro Ala Pro Lys Pro Lys Asn Ala Thr Val Leu Ile Trp
            100                 105                 110

Ile Tyr Gly Gly Gly Phe Gln Thr Gly Thr Ser Ser Leu His Val Tyr
        115                 120                 125

Asp Gly Lys Phe Leu Ala Arg Val Glu Arg Val Ile Val Val Ser Met
    130                 135                 140

Asn Tyr Arg Val Gly Ala Leu Gly Phe Leu Ala Leu Pro Gly Asn Pro
```

```
                145                 150                 155                 160
Glu Ala Pro Gly Asn Met Gly Leu Phe Asp Gln Gln Leu Ala Leu Gln
                165                 170                 175
Trp Val Gln Lys Asn Ile Ala Ala Phe Gly Asn Pro Lys Ser Val
            180                 185                 190
Thr Leu Phe Gly Glu Ser Ser Gly Ala Ala Ser Val Ser Leu His Leu
            195                 200                 205
Leu Ser Pro Gly Ser His Ser Leu Phe Thr Arg Ala Ile Leu Gln Ser
210                 215                 220
Gly Ser Leu Asn Ala Pro Trp Ala Val Thr Ser Leu Tyr Glu Ala Arg
225                 230                 235                 240
Asn Arg Thr Leu Asn Leu Ala Lys Leu Thr Gly Cys Ser Arg Glu Asn
                245                 250                 255
Glu Thr Glu Ile Ile Lys Cys Leu Arg Asn Lys Asp Pro Gln Glu Ile
                260                 265                 270
Leu Leu Asn Glu Ala Phe Val Val Pro Tyr Gly Thr Pro Leu Gly Val
            275                 280                 285
Asn Phe Gly Pro Thr Val Asp Gly Asp Phe Leu Thr Asp Met Pro Asp
            290                 295                 300
Ile Leu Leu Glu Leu Gly Gln Phe Lys Lys Thr Gln Ile Leu Val Gly
305                 310                 315                 320
Val Asn Lys Asp Glu Gly Thr Trp Phe Leu Val Gly Gly Ala Pro Gly
                325                 330                 335
Phe Ser Lys Asp Asn Asn Ser Ile Ile Thr Arg Lys Glu Phe Gln Glu
                340                 345                 350
Gly Leu Lys Ile Phe Phe Pro Gly Val Ser Glu Phe Gly Lys Glu Ser
            355                 360                 365
Ile Leu Phe His Tyr Thr Asp Trp Val Asp Asp Gln Arg Pro Glu Asn
            370                 375                 380
Tyr Arg Glu Ala Leu Gly Asp Val Val Gly Asp Tyr Asn Phe Ile Cys
385                 390                 395                 400
Pro Ala Leu Glu Phe Thr Lys Lys Phe Ser Glu Trp Gly Asn Asn Ala
                405                 410                 415
Phe Phe Tyr Tyr Phe Glu His Arg Ser Ser Lys Leu Pro Trp Pro Glu
                420                 425                 430
Trp Met Gly Val Met His Gly Tyr Glu Ile Glu Phe Val Phe Gly Leu
            435                 440                 445
Pro Leu Glu Arg Arg Asp Asn Tyr Thr Lys Ala Glu Glu Ile Leu Ser
            450                 455                 460
Arg Ser Ile Val Lys Arg Trp Ala Asn Phe Ala Lys Tyr Gly Asn Pro
465                 470                 475                 480
Asn Glu Thr Gln Asn Asn Ser Thr Ser Trp Pro Val Phe Lys Ser Thr
                485                 490                 495
Glu Gln Lys Tyr Leu Thr Leu Asn Thr Glu Ser Thr Arg Ile Met Thr
                500                 505                 510
Lys Leu Arg Ala Gln Gln Cys Arg Phe Trp Thr Ser Phe Phe Pro Lys
            515                 520                 525
Val Leu Glu Met Thr Gly Asn Ile Asp Glu Ala Glu Trp Glu Trp Lys
            530                 535                 540
Ala Gly Phe His Arg Trp Asn Asn Tyr Met Met Asp Trp Lys Asn Gln
545                 550                 555                 560
Phe Asn Asp Tyr Thr Ser Lys Lys Glu Ser Cys Val Gly Leu
                565                 570
```

<210> SEQ ID NO 29
<211> LENGTH: 1722
<212> TYPE: DNA
<213> ORGANISM: Artificial Sequence
<220> FEATURE:
<223> OTHER INFORMATION: mutant of human BChE

<400> SEQUENCE: 29

```
gaagatgaca tcataattgc aacaaagaat ggaaaagtca gagggatgaa cttgacagtt      60
tttggtggca cggtaacagc ctttcttgga attccctatg cacagccacc tcttggtaga     120
cttcgattca aaaagccaca gtctctgacc aagtggtctg atatttggaa tgccacaaaa     180
tatgcaaatt cttgctgtca aacatagat caaagttttc caggcttcca tggatcagag     240
atgtggaacc caaacactga cctcagtgaa gactgtttat atctaaatgt atggattcca     300
gcacctaaac aaaaaatgc cactgtattg atatggattt atggtggtgg ttttcaaact     360
ggaacatcat ctttacatgt ttatgatggc aagtttctgg ctcgggttga agagttatt     420
gtagtgtcaa tgaactatag ggtgggtgcc ctaggattct tagctttgcc aggaaatcct     480
gaggctccag ggaacatggg tttatttgat caacagttgg ctcttcagtg ggttcaaaaa     540
aatatagcag cctttggtgg aaatcctaaa agtgtaactc tctttggaga agttccgga     600
gcagcttcag ttagcctgca tttgctttct cctggaagcc attcattgtt caccagagcc     660
attctgcaaa gtggttcctt taatgctcct tgggcggtaa catctcttta tgaagctagg     720
aacagaacgt tgaacttagc taaattgact ggttgctcta gagagaatga gactgaaata     780
atcaagtgtc ttagaaataa agatccccaa gaaattcttc tgaatgaagc atttgttgtc     840
ccctatggga ctcctatggg tgtaaacttt ggtccgaccg tggatggtga ttttctcact     900
gacatgccag acatattact tgaacttgga caatttaaaa aaacccagat tttggtgggt     960
gttaataaag atgaagggac atggttttta gtcggtggtg ctcctggctt cagcaaagat    1020
aacaatagta tcataactag aaaagaattt caggaaggtt taaaatatat ttttccagga    1080
gtgagtgagt ttgaaaagga atccatcctt tttcattaca cagactggt agatgatcag    1140
agacctgaaa actaccgtga ggccttgggt gatgttgttg gggattataa tttcatatgc    1200
cctgccttgg agttcaccaa gaagttctca gaatggggaa ataatgcctt ttctactat    1260
tttgaacacc gatcctccaa acttccgtgg ccagaatgga tgggagtgat gcatggctat    1320
gaaattgaat ttgtctttgg tttacctctg gaaagaagag ataattacac aaaagccgag    1380
gaaattttga gtagatccat agtgaaacgg tgggcaaatt ttgcaaaata tgggaatcca    1440
aatgagactc agaacaatag cacaagctgg cctgtcttca aaagcactga acaaaaatat    1500
ctaaccttga atacagagtc aacaagaata atgacgaaac tacgtgctca acaatgtcga    1560
ttctggacat cattttttcc aaaagtcttg gaaatgacag aaatattga tgaagcagaa    1620
tgggagtgga agcaggatt ccatcgctgg aacaattaca tgatggactg gaaaaatcaa    1680
tttaacgatt acactagcaa gaaagaaagt tgtgtgggtc tc                       1722
```

<210> SEQ ID NO 30
<211> LENGTH: 574
<212> TYPE: PRT
<213> ORGANISM: Artificial Sequence
<220> FEATURE:
<223> OTHER INFORMATION: mutant of human BChE

<400> SEQUENCE: 30

-continued

```
Glu Asp Asp Ile Ile Ile Ala Thr Lys Asn Gly Lys Val Arg Gly Met
1               5                   10                  15

Asn Leu Thr Val Phe Gly Gly Thr Val Thr Ala Phe Leu Gly Ile Pro
            20                  25                  30

Tyr Ala Gln Pro Pro Leu Gly Arg Leu Arg Phe Lys Lys Pro Gln Ser
        35                  40                  45

Leu Thr Lys Trp Ser Asp Ile Trp Asn Ala Thr Lys Tyr Ala Asn Ser
    50                  55                  60

Cys Cys Gln Asn Ile Asp Gln Ser Phe Pro Gly Phe His Gly Ser Glu
65                  70                  75                  80

Met Trp Asn Pro Asn Thr Asp Leu Ser Glu Asp Cys Leu Tyr Leu Asn
                85                  90                  95

Val Trp Ile Pro Ala Pro Lys Pro Lys Asn Ala Thr Val Leu Ile Trp
            100                 105                 110

Ile Tyr Gly Gly Gly Phe Gln Thr Gly Thr Ser Ser Leu His Val Tyr
        115                 120                 125

Asp Gly Lys Phe Leu Ala Arg Val Glu Arg Val Ile Val Val Ser Met
    130                 135                 140

Asn Tyr Arg Val Gly Ala Leu Gly Phe Leu Ala Leu Pro Gly Asn Pro
145                 150                 155                 160

Glu Ala Pro Gly Asn Met Gly Leu Phe Asp Gln Gln Leu Ala Leu Gln
                165                 170                 175

Trp Val Gln Lys Asn Ile Ala Ala Phe Gly Gly Asn Pro Lys Ser Val
            180                 185                 190

Thr Leu Phe Gly Glu Ser Ser Gly Ala Ala Ser Val Ser Leu His Leu
        195                 200                 205

Leu Ser Pro Gly Ser His Ser Leu Phe Thr Arg Ala Ile Leu Gln Ser
    210                 215                 220

Gly Ser Phe Asn Ala Pro Trp Ala Val Thr Ser Leu Tyr Glu Ala Arg
225                 230                 235                 240

Asn Arg Thr Leu Asn Leu Ala Lys Leu Thr Gly Cys Ser Arg Glu Asn
                245                 250                 255

Glu Thr Glu Ile Ile Lys Cys Leu Arg Asn Lys Asp Pro Gln Glu Ile
            260                 265                 270

Leu Leu Asn Glu Ala Phe Val Val Pro Tyr Gly Thr Pro Met Gly Val
        275                 280                 285

Asn Phe Gly Pro Thr Val Asp Gly Asp Phe Leu Thr Asp Met Pro Asp
    290                 295                 300

Ile Leu Leu Glu Leu Gly Gln Phe Lys Lys Thr Gln Ile Leu Val Gly
305                 310                 315                 320

Val Asn Lys Asp Glu Gly Thr Trp Phe Leu Val Gly Gly Ala Pro Gly
                325                 330                 335

Phe Ser Lys Asp Asn Asn Ser Ile Ile Thr Arg Lys Glu Phe Gln Glu
            340                 345                 350

Gly Leu Lys Ile Phe Phe Pro Gly Val Ser Glu Phe Gly Lys Glu Ser
        355                 360                 365

Ile Leu Phe His Tyr Thr Asp Trp Val Asp Asp Gln Arg Pro Glu Asn
    370                 375                 380

Tyr Arg Glu Ala Leu Gly Asp Val Val Gly Asp Tyr Asn Phe Ile Cys
385                 390                 395                 400

Pro Ala Leu Glu Phe Thr Lys Lys Phe Ser Glu Trp Gly Asn Asn Ala
                405                 410                 415

Phe Phe Tyr Tyr Phe Glu His Arg Ser Ser Lys Leu Pro Trp Pro Glu
```

```
                          420              425              430
    Trp Met Gly Val Met His Gly Tyr Glu Ile Glu Phe Val Phe Gly Leu
                    435              440              445

Pro Leu Glu Arg Arg Asp Asn Tyr Thr Lys Ala Glu Glu Ile Leu Ser
                450              455              460

Arg Ser Ile Val Lys Arg Trp Ala Asn Phe Ala Lys Tyr Gly Asn Pro
    465              470              475              480

Asn Glu Thr Gln Asn Asn Ser Thr Ser Trp Pro Val Phe Lys Ser Thr
                            485              490              495

Glu Gln Lys Tyr Leu Thr Leu Asn Thr Glu Ser Thr Arg Ile Met Thr
                    500              505              510

Lys Leu Arg Ala Gln Gln Cys Arg Phe Trp Thr Ser Phe Phe Pro Lys
                515              520              525

Val Leu Glu Met Thr Gly Asn Ile Asp Glu Ala Glu Trp Glu Trp Lys
                530              535              540

Ala Gly Phe His Arg Trp Asn Asn Tyr Met Met Asp Trp Lys Asn Gln
    545              550              555              560

Phe Asn Asp Tyr Thr Ser Lys Lys Glu Ser Cys Val Gly Leu
                            565              570

<210> SEQ ID NO 31
<211> LENGTH: 1722
<212> TYPE: DNA
<213> ORGANISM: Artificial Sequence
<220> FEATURE:
<223> OTHER INFORMATION: mutant of human BChE

<400> SEQUENCE: 31
gaagatgaca tcataattgc aacaaagaat ggaaaagtca gagggatgaa cttgacagtt      60
tttggtggca cggtaacagc cttcttgga attccctatg cacagccacc tcttggtaga     120
cttcgattca aaaagccaca gtctctgacc aagtggtctg atatttggaa tgccacaaaa    180
tatgcaaatt cttgctgtca gaacatagat caaagttttc caggcttcca tggatcagag    240
atgtggaacc caaacactga cctcagtgaa gactgtttat atctaaatgt atggattcca    300
gcacctaaac caaaaatgc cactgtattg atatggattt atggtggtgg tttcaaact     360 ggaacatcat ctttacatgt ttatgatggc aagtttctgg ctcgggttga aagagttatt    420
gtagtgtcaa tgaactatag ggtgggtgcc ctaggattct tagctttgcc aggaaatcct    480
gaggctccag ggaacatggg tttatttgat aacagttgg ctcttcagtg ggttcaaaaa     540
aatatagcag cctttggtgg aaatcctaaa agtgtaactc tctttggaga aagttccgga    600
gcagcttcag ttagcctgca tttgctttct cctggaagcc attcattgtt caccagagcc    660
attctgcaaa gtggttccgc taatgctcct tgggcggtaa catctcttta tgaagctagg    720
aacagaacgt tgaacttagc taaattgact ggttgctcta gagagaatga gactgaaata    780
atcaagtgtc ttagaaataa agatcccaa gaaattcttc tgaatgaagc atttgttgtc    840
ccctatggga ctaaattggg tgtaaacttt ggtccgaccg tggatggtga ttttctcact    900
gacatgccag acatattact tgaacttgga caatttaaaa aaacccagat ttggtgggt     960 gttaataaag atgaagggac atggtttta gtcggtggtg ctcctggctt cagcaaagat   1020
aacaatagta tcataactag aaaagaattt caggaaggtt aaaaatatt ttttccagga    1080 gtgagtgagt tggaaagga atccatcctt tttcattaca cagactgggt agatgatcag   1140
agacctgaaa actaccgtga ggccttgggt gatgttgttg gggattataa tttcatatgc   1200
```

-continued

```
cctgccttgg agttcaccaa gaagttctca gaatggggaa ataatgcctt tttctactat    1260
tttgaacacc gatcctccaa acttccgtgg ccagaatgga tgggagtgat gcatggctat    1320
gaaattgaat tgtctttgg tttacctctg gaaagaagag ataattacac aaaagccgag     1380
gaaattttga gtagatccat agtgaaacgg tgggcaaatt ttgcaaaata tgggaatcca    1440
aatgagactc agaacaatag cacaagctgg cctgtcttca aaagcactga acaaaaatat    1500
ctaaccttga atacagagtc aacaagaata atgacgaaac tacgtgctca acaatgtcga    1560
ttctggacat catttttcc aaaagtcttg gaaatgacag gaaatattga tgaagcagaa     1620
tgggagtgga aagcaggatt ccatcgctgg aacaattaca tgatggactg gaaaaatcaa    1680
tttaacgatt acactagcaa gaaagaaagt tgtgtgggtc tc                       1722
```

<210> SEQ ID NO 32
<211> LENGTH: 574
<212> TYPE: PRT
<213> ORGANISM: Artificial Sequence
<220> FEATURE:
<223> OTHER INFORMATION: mutant of human BChE

<400> SEQUENCE: 32

```
Glu Asp Asp Ile Ile Ile Ala Thr Lys Asn Gly Lys Val Arg Gly Met
1               5                   10                  15

Asn Leu Thr Val Phe Gly Gly Thr Val Thr Ala Phe Leu Gly Ile Pro
            20                  25                  30

Tyr Ala Gln Pro Pro Leu Gly Arg Leu Arg Phe Lys Lys Pro Gln Ser
        35                  40                  45

Leu Thr Lys Trp Ser Asp Ile Trp Asn Ala Thr Lys Tyr Ala Asn Ser
    50                  55                  60

Cys Cys Gln Asn Ile Asp Gln Ser Phe Pro Gly Phe His Gly Ser Glu
65                  70                  75                  80

Met Trp Asn Pro Asn Thr Asp Leu Ser Glu Asp Cys Leu Tyr Leu Asn
                85                  90                  95

Val Trp Ile Pro Ala Pro Lys Pro Lys Asn Ala Thr Val Leu Ile Trp
            100                 105                 110

Ile Tyr Gly Gly Gly Phe Gln Thr Gly Thr Ser Ser Leu His Val Tyr
        115                 120                 125

Asp Gly Lys Phe Leu Ala Arg Val Glu Arg Val Ile Val Val Ser Met
    130                 135                 140

Asn Tyr Arg Val Gly Ala Leu Gly Phe Leu Ala Leu Pro Gly Asn Pro
145                 150                 155                 160

Glu Ala Pro Gly Asn Met Gly Leu Phe Asp Gln Gln Leu Ala Leu Gln
                165                 170                 175

Trp Val Gln Lys Asn Ile Ala Ala Phe Gly Gly Asn Pro Lys Ser Val
            180                 185                 190

Thr Leu Phe Gly Glu Ser Ser Gly Ala Ala Ser Val Ser Leu His Leu
        195                 200                 205

Leu Ser Pro Gly Ser His Ser Leu Phe Thr Arg Ala Ile Leu Gln Ser
    210                 215                 220

Gly Ser Ala Asn Ala Pro Trp Ala Val Thr Ser Leu Tyr Glu Ala Arg
225                 230                 235                 240

Asn Arg Thr Leu Asn Leu Ala Lys Leu Thr Gly Cys Ser Arg Glu Asn
                245                 250                 255

Glu Thr Glu Ile Ile Lys Cys Leu Arg Asn Lys Asp Pro Gln Glu Ile
            260                 265                 270
```

-continued

```
Leu Leu Asn Glu Ala Phe Val Val Pro Tyr Gly Thr Lys Leu Gly Val
        275                 280                 285

Asn Phe Gly Pro Thr Val Asp Gly Asp Phe Leu Thr Asp Met Pro Asp
    290                 295                 300

Ile Leu Leu Glu Leu Gly Gln Phe Lys Lys Thr Gln Ile Leu Val Gly
305             310                 315                 320

Val Asn Lys Asp Glu Gly Thr Trp Phe Leu Val Gly Gly Ala Pro Gly
                325                 330                 335

Phe Ser Lys Asp Asn Asn Ser Ile Ile Thr Arg Lys Glu Phe Gln Glu
            340                 345                 350

Gly Leu Lys Ile Phe Phe Pro Gly Val Ser Glu Phe Gly Lys Glu Ser
        355                 360                 365

Ile Leu Phe His Tyr Thr Asp Trp Val Asp Asp Gln Arg Pro Glu Asn
    370                 375                 380

Tyr Arg Glu Ala Leu Gly Asp Val Val Gly Asp Tyr Asn Phe Ile Cys
385             390                 395                 400

Pro Ala Leu Glu Phe Thr Lys Lys Phe Ser Glu Trp Gly Asn Asn Ala
                405                 410                 415

Phe Phe Tyr Tyr Phe Glu His Arg Ser Ser Lys Leu Pro Trp Pro Glu
            420                 425                 430

Trp Met Gly Val Met His Gly Tyr Glu Ile Glu Phe Val Phe Gly Leu
        435                 440                 445

Pro Leu Glu Arg Arg Asp Asn Tyr Thr Lys Ala Glu Glu Ile Leu Ser
    450                 455                 460

Arg Ser Ile Val Lys Arg Trp Ala Asn Phe Ala Lys Tyr Gly Asn Pro
465             470                 475                 480

Asn Glu Thr Gln Asn Asn Ser Thr Ser Trp Pro Val Phe Lys Ser Thr
                485                 490                 495

Glu Gln Lys Tyr Leu Thr Leu Asn Thr Glu Ser Thr Arg Ile Met Thr
            500                 505                 510

Lys Leu Arg Ala Gln Gln Cys Arg Phe Trp Thr Ser Phe Phe Pro Lys
        515                 520                 525

Val Leu Glu Met Thr Gly Asn Ile Asp Glu Ala Glu Trp Glu Trp Lys
    530                 535                 540

Ala Gly Phe His Arg Trp Asn Asn Tyr Met Met Asp Trp Lys Asn Gln
545             550                 555                 560

Phe Asn Asp Tyr Thr Ser Lys Lys Glu Ser Cys Val Gly Leu
                565                 570
```